(12) United States Patent
Takashino et al.

(10) Patent No.: US 10,363,083 B2
(45) Date of Patent: Jul. 30, 2019

(54) ENERGY TREATMENT SYSTEM, ENERGY CONTROL DEVICE, AND ENERGY TREATMENT INSTRUMENT

(71) Applicant: OLYMPUS CORPORATION, Hachioji-shi, Tokyo (JP)

(72) Inventors: Tomoyuki Takashino, Fuchu (JP); Yusuke Takei, Hino (JP); Kazuhiro Tanaka, Hachioji (JP)

(73) Assignee: OLYMPUS CORPORATION, Tokyo (JP)

( * ) Notice: Subject to any disclaimer, the term of this patent is extended or adjusted under 35 U.S.C. 154(b) by 31 days.

(21) Appl. No.: 15/603,574

(22) Filed: May 24, 2017

(65) Prior Publication Data

US 2017/0252087 A1 Sep. 7, 2017

Related U.S. Application Data

(63) Continuation of application No. PCT/JP2016/070582, filed on Jul. 12, 2016.

(30) Foreign Application Priority Data

Jul. 24, 2015 (JP) ................. 2015-146722

(51) Int. Cl.
*A61B 18/08* (2006.01)
*A61B 18/12* (2006.01)
(Continued)

(52) U.S. Cl.
CPC .......... *A61B 18/085* (2013.01); *A61B 5/0537* (2013.01); *A61B 5/0538* (2013.01);
(Continued)

(58) Field of Classification Search
CPC ................ G01N 27/048; A61B 18/085; A61B 5/0537; A61B 5/4875; A61B 2018/00875;
(Continued)

(56) References Cited

U.S. PATENT DOCUMENTS

| | | |
|---|---|---|
| 2001/0037109 A1 | 11/2001 | Yamauchi et al. |
| 2002/0082593 A1 | 6/2002 | Hareyama et al. |

(Continued)

FOREIGN PATENT DOCUMENTS

| | | |
|---|---|---|
| JP | 2008-023335 A | 2/2008 |
| JP | 2009-247893 A | 10/2009 |

(Continued)

OTHER PUBLICATIONS

Oct. 18, 2016 International Search Report issued in Patent Application No. PCT/JP2016/070582.

(Continued)

*Primary Examiner* — Michael F Peffley
*Assistant Examiner* — Yasamin Ekrami
(74) *Attorney, Agent, or Firm* — Oliff PLC

(57) ABSTRACT

An energy output section outputs first electric energy so that a high-frequency current flows between electrodes through a treated target, and outputs second electric energy so that heat occurs in an end effector. A controller outputs the first electric energy at the same time as the second electric energy in at least a part of a period during which the heat is continuously denaturing the treated target from an output start of the second electric energy. The controller makes, based on judging that the treated target entered a predetermined state, an electric power of the first electric energy increased.

16 Claims, 14 Drawing Sheets

(51) Int. Cl.
*A61B 5/053* (2006.01)
*A61B 5/00* (2006.01)
*A61B 18/14* (2006.01)
*G01N 27/04* (2006.01)
*A61B 18/10* (2006.01)
*A61B 17/00* (2006.01)
*A61B 18/00* (2006.01)

(52) U.S. Cl.
CPC .......... *A61B 5/4836* (2013.01); *A61B 5/4875* (2013.01); *A61B 5/6847* (2013.01); *A61B 18/08* (2013.01); *A61B 18/10* (2013.01); *A61B 18/12* (2013.01); *A61B 18/1445* (2013.01); *A61B 18/1447* (2013.01); *G01N 27/048* (2013.01); *A61B 2017/0003* (2013.01); *A61B 2017/00026* (2013.01); *A61B 2017/00084* (2013.01); *A61B 2018/00654* (2013.01); *A61B 2018/00702* (2013.01); *A61B 2018/00714* (2013.01); *A61B 2018/00875* (2013.01); *A61B 2018/00994* (2013.01)

(58) Field of Classification Search
CPC .......... A61B 2018/00654; A61B 2018/00714; A61B 2018/00994; A61B 2018/00702
See application file for complete search history.

(56) References Cited

U.S. PATENT DOCUMENTS

| | | |
|---|---|---|
| 2008/0015575 A1 | 1/2008 | Odom et al. |
| 2009/0076506 A1 | 3/2009 | Baker |
| 2009/0248002 A1* | 10/2009 | Takashino ............ A61B 18/085 606/28 |
| 2009/0299367 A1* | 12/2009 | Ginnebaugh ........ A61B 18/085 606/51 |
| 2010/0185196 A1 | 7/2010 | Sakao et al. |
| 2011/0077629 A1 | 3/2011 | Tanaka et al. |
| 2011/0077630 A1 | 3/2011 | Tanaka et al. |
| 2014/0207135 A1* | 7/2014 | Winter ............... A61B 18/1445 606/40 |

FOREIGN PATENT DOCUMENTS

| | | |
|---|---|---|
| JP | 2010-538796 A | 12/2010 |
| JP | 2012-165948 A | 9/2012 |
| WO | 2010/084683 A1 | 7/2010 |
| WO | 2013/088890 A1 | 6/2013 |
| WO | 2015/077119 A1 | 5/2015 |

OTHER PUBLICATIONS

Feb. 8, 2018 Translation of IPRP and Written Opinion issued in International Application No. PCT/JP2016/070582.
Feb. 11, 2019 extended European Search Report issued in European Application No. 16830310.5.
Feb. 19, 2019 Office Action issued in Chinese Application No. 201680004833.2.

* cited by examiner

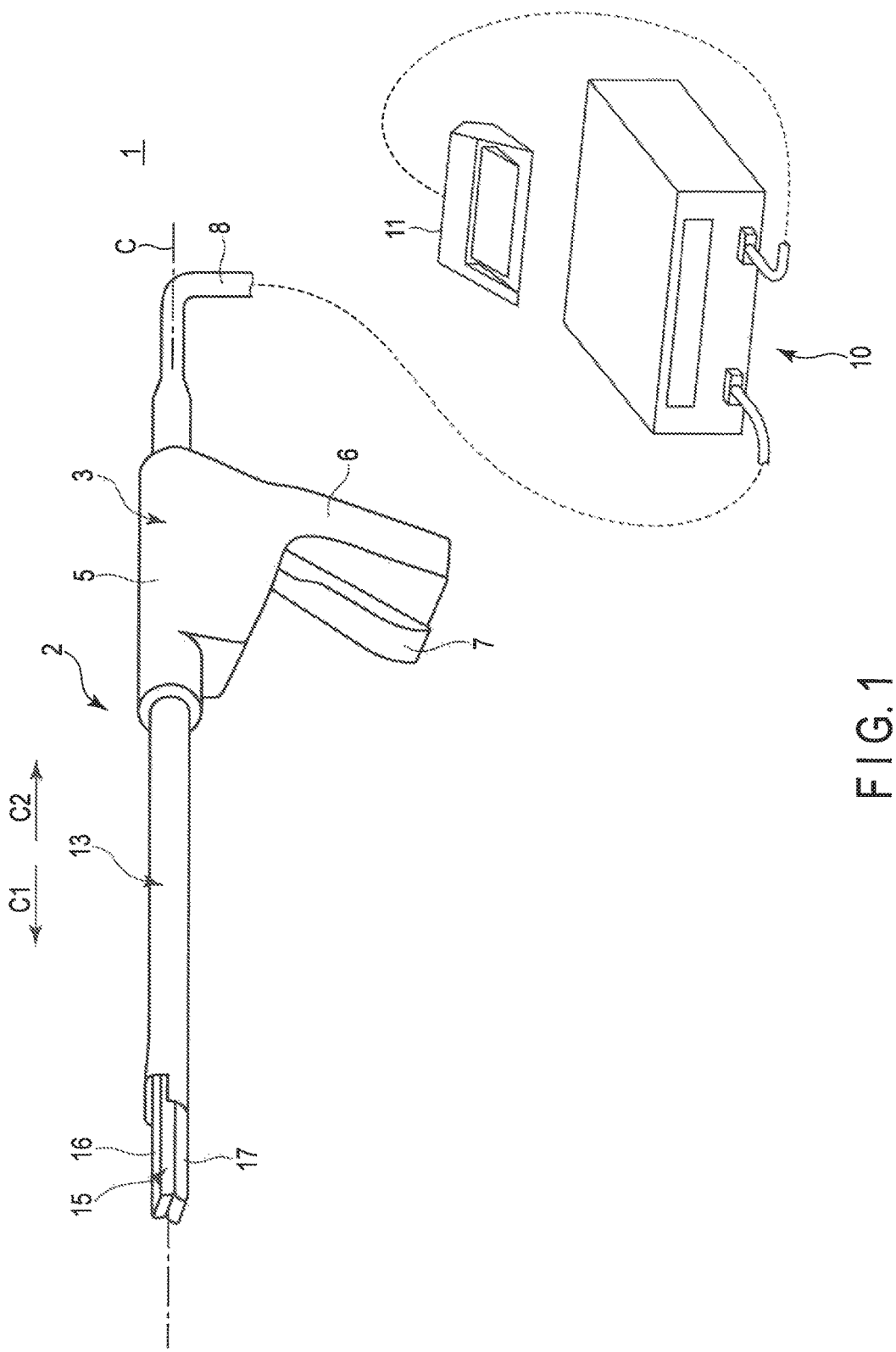
F I G. 1

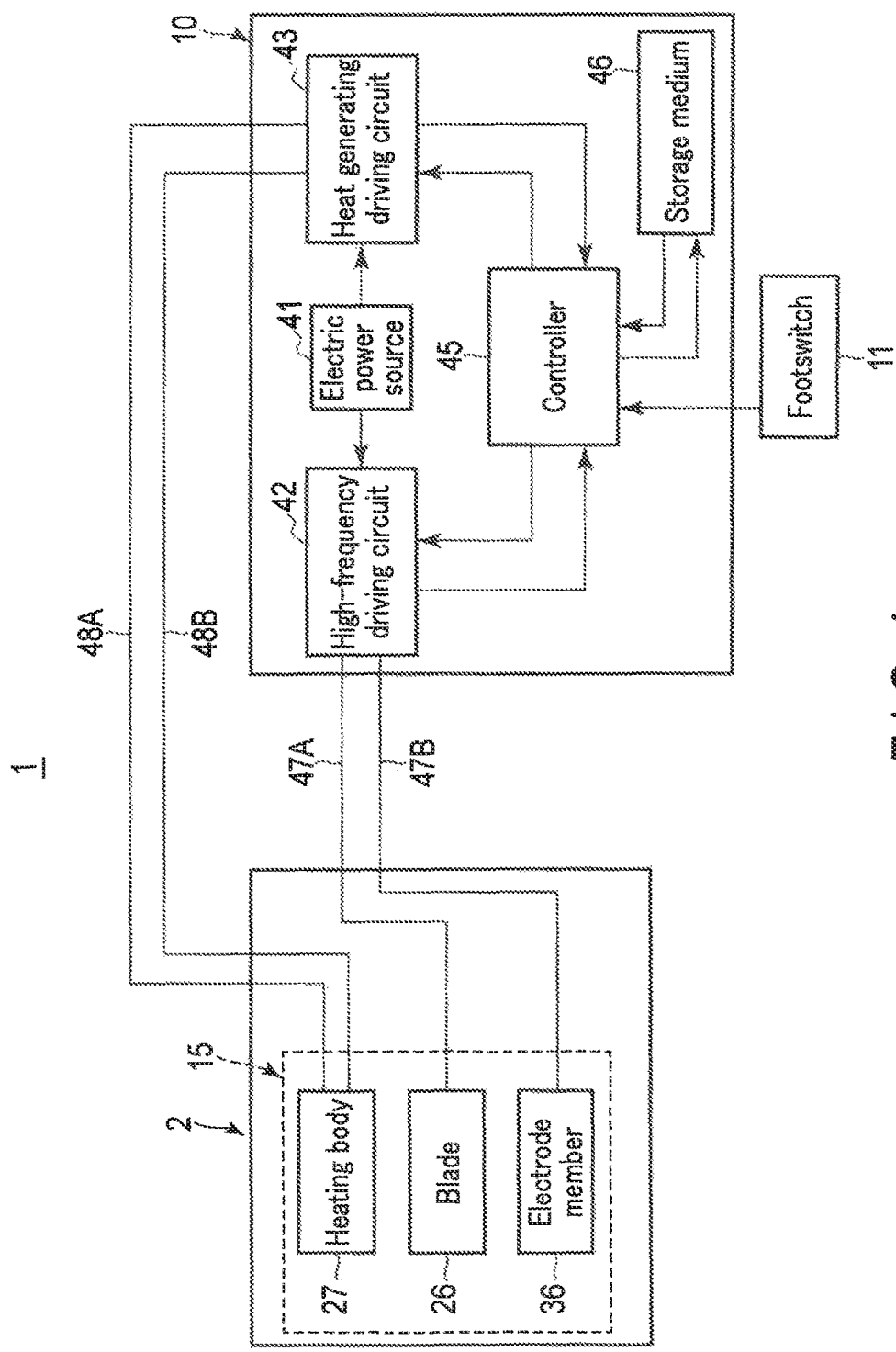
F I G. 4

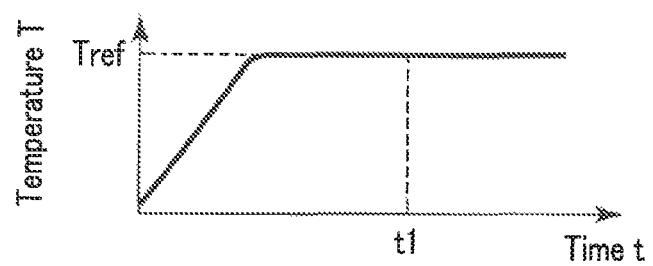
F I G. 6A
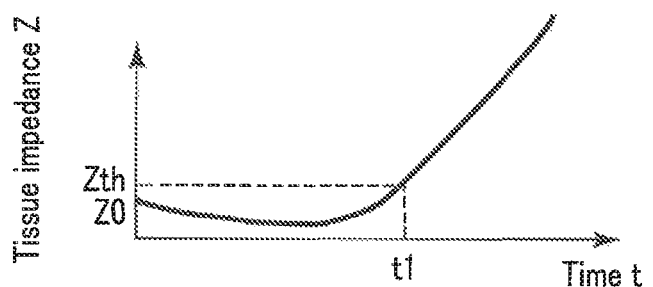
F I G. 6B

| Pattern | Judgment parameter | Condition for judgment of entering predetermined state |
|---|---|---|
| X1 | Tissue impedance Z | $Z(t) \geq Z_{th}$ |
| X2 | Change rate $\varepsilon$ of tissue impedance Z and count time Y | $\varepsilon(t) > 0$ And $Y \geq Y_{ref}$ |
| X3 | Phase difference $\Phi$ between high-frequency current I and high-frequency voltage V | $|\Phi(t) - \Phi(0)| \geq \Phi_{th}$ |
| X4 | Resistance value R of heating body 27 | $R(t) \geq R_{th}$ |
| X5 | Change rate $\gamma$ of resistance value R and count time U | $|\gamma(t)| \leq \gamma_{th}$ And $U \geq U_{ref}$ |
| X6 | Temperature T of grasping surface Z1 | $T(t) \geq T_{th}$ |
| X7 | Change rate $\gamma'$ of temperature T and count time U' | $|\gamma'(t)| \leq \gamma'_{th}$ And $U' \geq U'_{ref}$ |
| X8 | Water content amount $\sigma$ of treated target | $\sigma(t) \leq \sigma_{th}$ |
| X9 | Opening angle $\alpha$ between clamps 16 and 17 | $\alpha(t) \leq \alpha_{th}$ |
| X10 | Time t with reference to output start | $t \geq t_a$ |
| X11 | Integration value W of high-frequency electric power P | $W(t) \geq W_{th}$ |
| X12 | Integration value W'A of heat generating electric power P'A | $W'A(t) \geq W'A_{th}$ |

FIG. 9

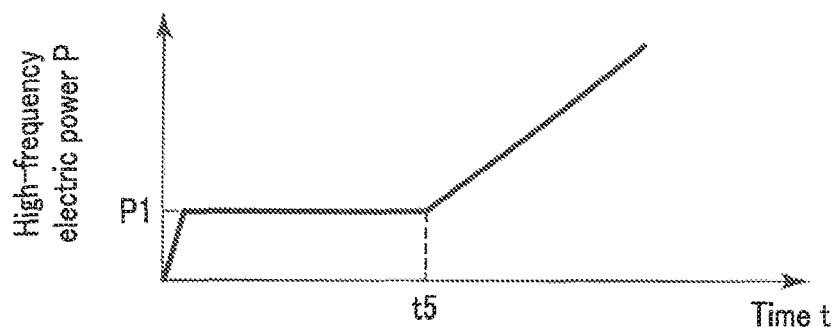
F I G. 11A
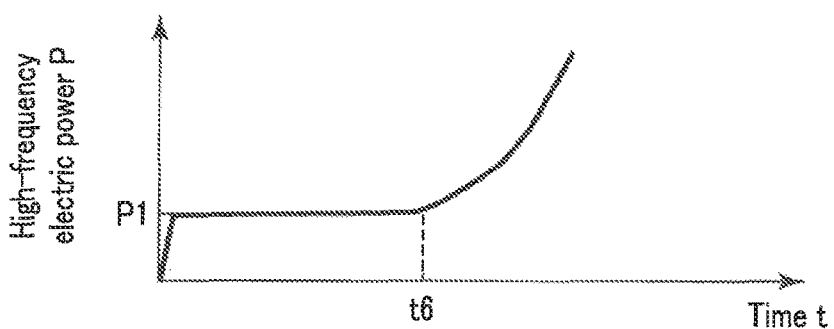
F I G. 11B
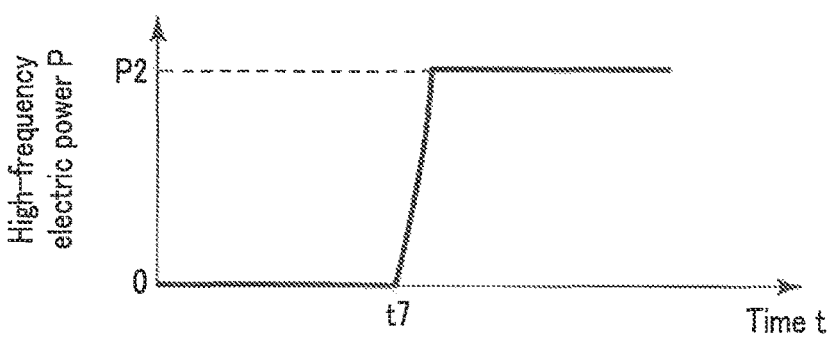
F I G. 11C

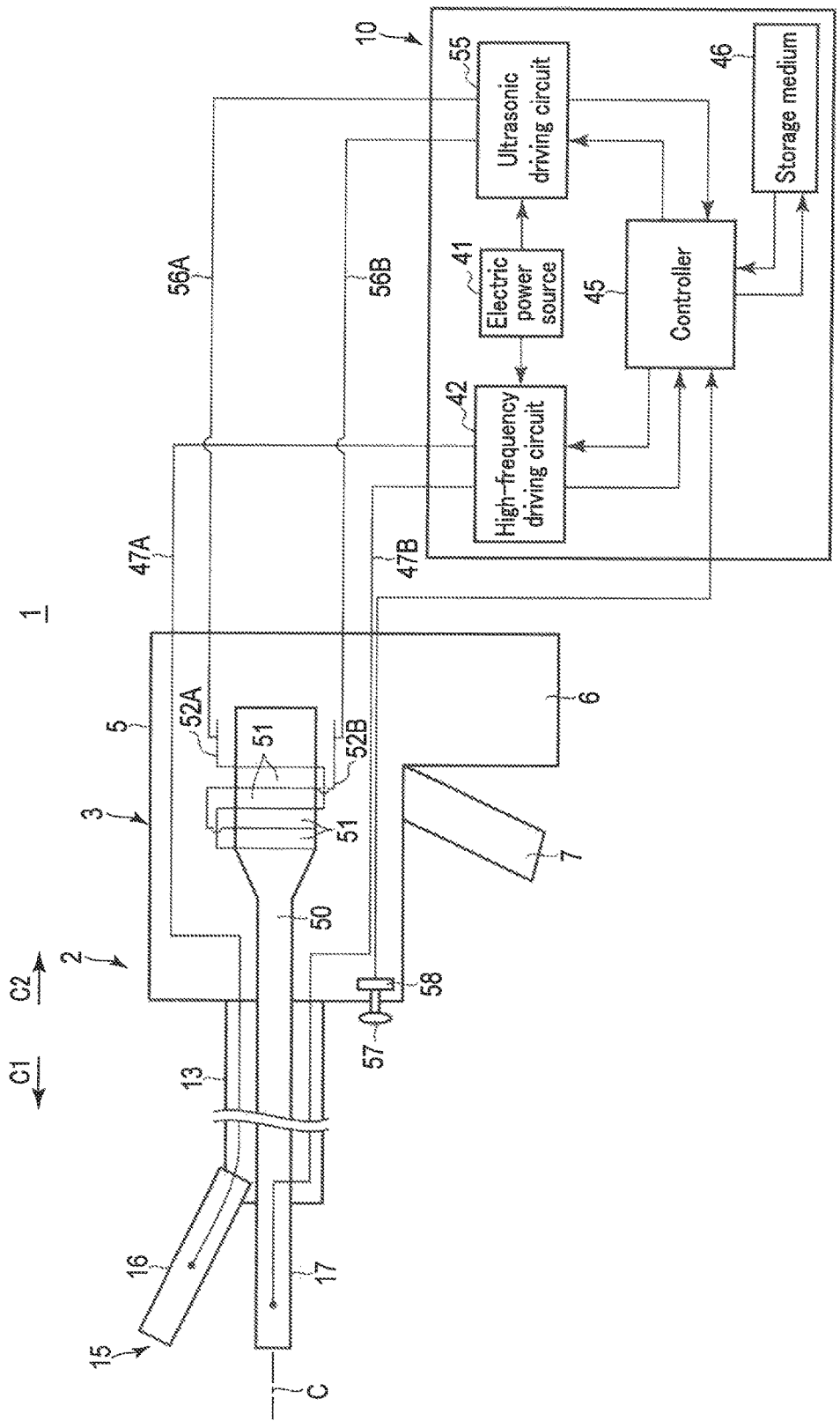
F I G. 12

ENERGY TREATMENT SYSTEM, ENERGY CONTROL DEVICE, AND ENERGY TREATMENT INSTRUMENT

CROSS-REFERENCE TO RELATED APPLICATIONS

This is a Continuation Application of PCT Application No. PCT/JP2016/070582, filed Jul. 12, 2016 and based upon and claiming the benefit of priority from prior Japanese Patent Application No. 2015-146722, filed Jul. 24, 2015, the entire contents of which are incorporated herein by reference.

BACKGROUND OF THE INVENTION

1. Field of the Invention

The present invention relates to an energy treatment system in which energy is supplied from an energy control device to an energy treatment instrument, and an end effector, which is provided in the energy treatment instrument, treats a treated target by using the supplied energy. In addition, the invention relates to an energy control device and an energy treatment instrument, which are provided in this energy treatment system.

2. Description of the Related Art

U.S. Patent Application Publication No. 2009/248002 discloses an energy treatment instrument which is provided with an end effector that grasps a treated target between two (a pair of) clamps. In this energy treatment instrument, an electrode is provided in each of the clamps, and high-frequency electric energy (first electric energy) is supplied from an energy control device to the electrodes. Thereby, a high-frequency current flows between the electrodes through a treated target that is grasped, and the treated target is denatured. In addition, in the end effector, a heating body is provided in one of the clamps, and heat generating electric energy (second electric energy) is supplied to the heating body. Thereby, heat is generated in the heating body. When the output of the high-frequency electric energy is started, the output of the heat generating electric energy is stopped, or the output of the heat generating electric energy is controlled in such a state that the temperature of the heating body does not rise to such a degree as to denature the treated target. In addition, if the output of the high-frequency electric energy is started, a tissue impedance of the treated target is detected with the passing of time. Based on the tissue impedance reaching a threshold value or above, the electric power of the heat generating electric energy is made greater than before the tissue impedance reaches the threshold value. Thereby, the temperature of the heating body rises up to such a degree as to denature the treated target, and the treated target is denatured by the heat generated in the heating body. By using the high-frequency current and the heat generated in the heating body, the treated target is denatured, and thereby the treated target is coagulated and sealed.

BRIEF SUMMARY OF THE INVENTION

According to one aspect of the invention, an energy treatment system including: an end effector including a pair of clamps which are openable and closable relative to each other, the end effector being configured to be capable of grasping a treated target between the clamps, each of the clamps including an electrode; an energy output section configured to be capable of outputting first electric energy and second electric energy, configured to pass a high-frequency current between the electrodes through the treated target grasped between the clamps by supplying the first electric energy to the electrodes of the end effector, and configured to actuate the end effector so as to generate, in the end effector, heat for use in a treatment of the treated target by outputting the second electric energy; and a controller configured to control outputs of the first electric energy and the second electric energy from the energy output section, configured to continuously output the second electric energy from the energy output section in such a state that the treated target is continuously denatured from an output start of the second electric energy by the heat generated by an actuation of the end effector, configured to output the first electric energy from the energy output section at the same time as the second electric energy in at least a part of a period during which the heat generated by the output of the second electric energy is continuously denaturing the treated target, and configured to make, based on judging that the treated target entered a predetermined state in a state in which the heat is continuously denaturing the treated target, an electric power of the first electric energy greater than before a time point of a judgment that the treated target entered the predetermined state.

According to one another aspect of the invention, an energy control device configured to control a supply of energy to an energy treatment instrument, the energy instrument being provided with an end effector including a pair of clamps which are openable and closable relative to each other, the end effector being configured to be capable of grasping a treated target between the clamps, each of the clamps including an electrode, the energy control device including: an energy output section configured to be capable of outputting first electric energy and second electric energy, configured to pass a high-frequency current between the electrodes through the treated target grasped between the clamps by supplying the first electric energy to the electrodes of the end effector, and configured to actuate the end effector so as to generate, in the end effector, heat for use in a treatment of the treated target by outputting the second electric energy; and a controller configured to control outputs of the first electric energy and the second electric energy from the energy output section, configured to continuously output the second electric energy from the energy output section in such a state that the treated target is continuously denatured from an output start of the second electric energy by the heat generated by an actuation of the end effector, configured to output the first electric energy from the energy output section at the same time as the second electric energy in at least a part of a period during which the heat generated by the output of the second electric energy is continuously denaturing the treated target, and configured to make, based on judging that the treated target entered a predetermined state in a state in which the heat is continuously denaturing the treated target, an electric power of the first electric energy greater than before a time point of a judgment that the treated target entered the predetermined state.

According to one another aspect of the invention, an energy treatment instrument which is supplied with energy from an energy control device, the energy control device including an energy output section configured to be capable of outputting first electric energy and second electric energy, and a controller configured to control outputs of the first electric energy and the second electric energy from the energy output section, the energy treatment instrument including: an end effector including a pair of clamps which are openable and closable relative to each other, the end effector being configured to be capable of grasping a treated target between the clamps, each of the clamps including an electrode, wherein the electrodes of the end effector are supplied with the first electric energy from the energy output section, thereby passing a high-frequency current between the electrodes through the treated target grasped between the clamps, the energy treatment instrument is supplied with the second electric energy from the energy output section, thereby actuating the end effector, and generating, in the end effector, heat for use in a treatment of the treated target, in the end effector, by the second electric energy being continuously output from the energy output section, the treated target is continuously denatured from an output start of the second electric energy by the heat generated by an actuation of the end effector, the energy treatment instrument is supplied with the first electric energy at the same time as the second electric energy from the energy output section, in at least a part of a period during which the heat generated by the supply of the second electric energy is continuously denaturing the treated target, and in the electrodes of the end effector, based on the controller judging that the treated target entered a predetermined state in a state in which the heat is continuously denaturing the treated target, an electric power of the first electric energy supplied from the energy output section is made greater than before a time point of a judgment that the treated target entered the predetermined state.

Advantages of the invention will be set forth in the description which follows, and in part will be obvious from the description, or may be learned by practice of the invention. The advantages of the invention may be realized and obtained by means of the instrumentalities and combinations particularly pointed out hereinafter.

BRIEF DESCRIPTION OF THE SEVERAL VIEWS OF THE DRAWING

The accompanying drawings, which are incorporated in and constitute a part of the specification, illustrate embodiments of the invention, and together with the general description given above and the detailed description of the embodiments given below, serve to explain the principles of the invention.

FIG. 1 is a perspective view which schematically illustrates an energy treatment system according to a first embodiment, FIG. 4 is a schematic view illustrating a configuration which supplies energy from an energy control device to the energy treatment instrument according to the first embodiment, FIG. 6A is a schematic view illustrating an example of a variation with time of a temperature of a grasping surface in a case in which the output of energy is controlled by the energy control device according to the first embodiment, FIG. 6B is a schematic view illustrating an example of a variation with time of a tissue impedance in a case in which the output of energy is controlled by the energy control device according to the first embodiment, FIG. 9 is a schematic view illustrating patterns of judgment parameters and judgment conditions at a time when it is judged whether a treated target entered a predetermined condition or not, by controllers according to the first embodiment, second embodiment and modifications thereof, FIG. 11A is a schematic view illustrating an example of a variation with time of high-frequency electric power in a case in which the output of energy is controlled by an energy control device according to a second modification of the first embodiment and second embodiment, FIG. 11B is a schematic view illustrating an example of a variation with time of high-frequency electric power in a case in which the output of energy is controlled by an energy control device according to a third modification of the first embodiment and second embodiment, FIG. 11C is a schematic view illustrating an example of a variation with time of high-frequency electric power in a case in which the output of energy is controlled by an energy control device according to a fourth modification of the first embodiment and second embodiment, FIG. 12 is a schematic view illustrating an energy treatment system according to a third embodiment.

Figure 2:
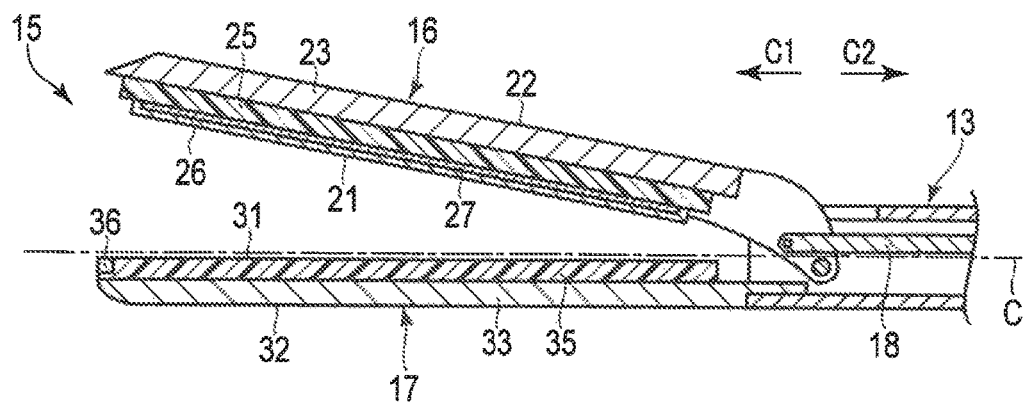
FIG. 2 is a cross-sectional view which schematically illustrates the configuration of a distal portion of an energy treatment instrument according to the first embodiment, by a cross section perpendicular to a width direction of an end effector.

DETAILED DESCRIPTION OF THE INVENTION (First Embodiment)

A first embodiment of the present invention will be described with reference to FIG. 1 to FIG. 6D.

FIG. 1 is a view illustrating an energy treatment system (bipolar treatment system) 1 in which an energy treatment instrument (bipolar treatment instrument) 2 of the present embodiment is used. As illustrated in FIG. 1, the energy treatment instrument (forceps treatment instrument) 2 has a longitudinal axis C. Here, one side of a direction along the longitudinal axis C is a distal side (an arrow C1 side in FIG. 1), and a side opposite to the distal side is a proximal side (an arrow C2 side in FIG. 1).

The energy treatment instrument 2 includes a housing 3 which can be held. The housing 3 includes a housing body 5 which extends along the longitudinal axis C, and a grip (stationary handle) 6 which extends from the housing body 5 in a direction crossing the longitudinal axis C. In addition, a handle (movable handle) 7 is rotatably attached to the housing 3. By the handle 7 rotating relative to the housing 3, the handle 7 opens or closes relative to the grip 6.

One end of a cable 8 is connected to a proximal portion of the housing body 5 of the housing 3. The other end of the cable 8 is detachably attached to an energy control device 10. A footswitch 11, which functions as an operation input section, is electrically connected to the energy control device 10. The energy control device 10 controls the supply of energy to the energy treatment instrument 2, based on an operation input or the like in the footswitch 11. Incidentally, the operation input section is not limited to the footswitch 11, and may be, for instance, an operation button which is attached to the housing 3.

A cylindrical shaft 13 is coupled to the housing body 5 from the distal side. The shaft 13 extends along the longitudinal axis C, and an end effector 15 is coupled to a distal portion of the shaft 13. The end effector 15 includes a first clamp 16 and a second clamp 17. The paired clamps 16 and 17 are openable and closable relative to each other, and a treated target can be grasped between the first clamp 16 and second clamp 17.

Figure 3:
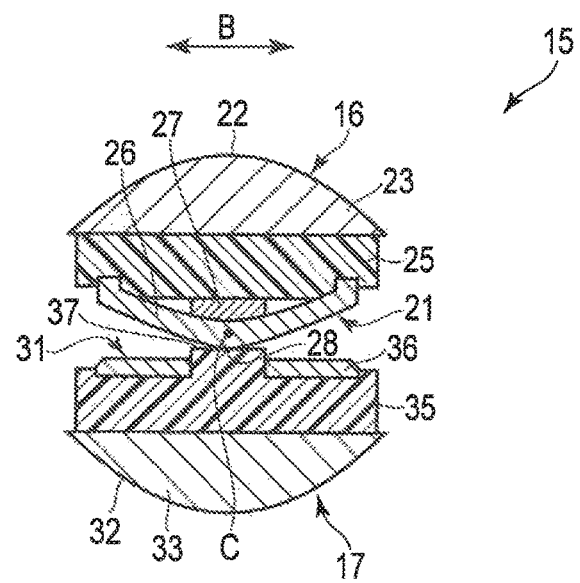
FIG. 3 is a cross-sectional view which schematically illustrates the end effector according to the first embodiment by a cross section perpendicular to a longitudinal axis.

FIG. 2 is a view illustrating the configuration of a distal portion of the energy treatment instrument 2 including the end effector 15, by a cross section substantially perpendicular to a width direction of the end effector 15 (a cross section substantially parallel to the longitudinal axis C). FIG. 3 is a view illustrating the end effector 15 by a cross section substantially perpendicular to the longitudinal axis C. FIG. 2 illustrates a state in which the paired clamps 16 and 17 are opened relative to each other, and FIG. 3 illustrates a state in which the paired clamps 16 and 17 are closed relative to each other. As illustrated in FIG. 2 and FIG. 3, a rod 18 extends in the inside of the shaft 13 along the longitudinal axis C. By opening or closing the handle 7 relative to the grip 6, the rod 18 moves relative to the shaft 13 along the longitudinal axis C. Thereby, the clamps 16 and 17 are opened or closed relative to each other. Incidentally, the width direction of the end effector 15 is a direction perpendicular to the sheet surface of FIG. 2, and is a direction of an arrow B in FIG. 3.

The first clamp 16 includes a support member (first support member) 23 which is rotatably coupled to the distal portion of the shaft 13. A distal end of the rod 18 is connected to the support member 23. An outer surface (exposed surface) of the first clamp 16 is provided with a grasping surface (first grasping surface) 21 which is opposed to the second clamp 17, and a back surface (first back surface) 22 which faces a side opposite to the grasping surface 21. In a state in which a treated target is grasped between the paired clamps 16 and 17, the grasping surface (first grasping surface) 21 in the first clamp 16 comes in contact with the treated target. In the first clamp 16, a relay member 25 having adiathermancy and electrical insulativeness is attached to the grasping surface 21 side (the side toward the second clamp 17) with respect to the support member 23, and a blade (first electrode) 26 having high thermal conductivity and having electrical conductivity is attached to the grasping surface 21 side with respect to the relay member 25. In addition, a heating body 27, such as a heater, is provided between the blade 26 and relay member 25. Accordingly, in the first clamp 16, the heating body 27 is provided on the back surface 22 side (the side away from the second clamp 17) with respect to the blade 26. In addition, in the first clamp 16, the back surface 22 is formed by the support member 23, and the grasping surface 21 is formed by the blade (first electrode) 26. The support member 23, relay member 25, blade 26 and heating body 27 extend from the proximal portion to distal portion of the first clamp 16 in the direction along the longitudinal axis C. Besides, on the grasping surface 21 of the first clamp 16, a ridge portion 28 is formed by the blade 26. The ridge portion 28 extends on the grasping surface 21 from the proximal portion to distal portion of the first clamp 16.

The second clamp 17 includes a support member (second support member) 33 which is coupled to the distal portion of the shaft 13 in the state in which the support member (second support member) 33 is fixed to the shaft 13. An outer surface (exposed surface) of the second clamp 17 is provided with a grasping surface (second grasping surface) 31 which is opposed to the first clamp 16 (the grasping surface 21 of the first clamp 16), and a back surface (second back surface) 32 which faces a side opposite to the grasping surface 31. In the state in which the treated target is grasped between the paired clamps 16 and 17, the grasping surface (second grasping surface) 31 in the second clamp 17 comes in contact with the treated target. In the second clamp 17, a receiving member 35 having adiathermancy and electrical insulativeness is attached to the grasping surface 31 side (the side toward the first clamp 16) with respect to the support member 33, and an electrode member (second electrode) 36 having electrical conductivity is attached to the receiving member 35. In the second clamp 17, the back surface 32 is formed by the support member 33, and the grasping surface 31 is formed by the receiving member 35 and electrode member (second electrode) 36. The support member 33, receiving member 35 and electrode member 36 extend from the proximal portion to distal portion of the second clamp 17 in the direction along the longitudinal axis C. Besides, on the grasping surface 31 of the second clamp 17, a receiving surface 37 is formed by the receiving member 35. The receiving surface 37 extends on the grasping surface 31 from the proximal portion to distal portion of the second clamp 17. In the state in which the paired clamps 16 and 17 are closed relative to each other, the ridge portion 28 of the first clamp 16 (blade 26) can abut on the receiving surface 37 of the second clamp 17 (receiving member 35). In addition, in the state in which the ridge portion 28 abuts on the receiving surface 37, the blade (first electrode) 26 of the first clamp 16 does not come in contact with the electrode member (second electrode) 36 of the second clamp 17.

In the meantime, in the present embodiment, the first clamp 16 is rotatable relative to the shaft 13, and the second clamp 17 is fixed to the shaft 13. However, the restriction to this is unnecessary. For example, the first clamp 16, which is provided with the heating body 27, may be fixed to the shaft 13, and the second clamp 17 may be rotatably attached to the shaft 13. Besides, by the rod 18 moving along the longitudinal axis C, both the clamps 16 and 17 may rotate, and the clamps 16 and 17 may open or close relative to each other.

FIG. 4 is a view illustrating a configuration which supplies energy from the energy control device 10 to the energy treatment instrument 2. As illustrated in FIG. 4, the energy control device 10 includes an electric power source 41 which is, for instance, a plug socket or a battery. In addition, the energy control device 10 includes a high-frequency driving circuit 42 which functions as an energy output section that can output high-frequency electric energy (first electric energy); and a heat generating driving circuit 43 which functions as an energy output section that can output heat generating electric energy (second electric energy). The high-frequency driving circuit 42 includes a converter circuit which converts electric power from the electric power source 41 to high-frequency electric energy, and the heat generating driving circuit 43 includes a converter circuit which converts electric power from the electric power source 41 to heat generating electric energy. Incidentally, high-frequency electric power P, which is output as the high-frequency electric energy, is AC electric power, and heat generating electric power P'A, which is output as the heat generating electric energy, is DC electric power or AC electric power.

The energy control device 10 includes a controller 45, and a storage medium 46 such as a memory. The controller 45 includes a processor including, for example, a CPU (Central Processing Unit) or an ASIC (application specific integrated circuit), and is composed of electronic circuitry provided in the processor. In addition, the controller 45 may be formed of a single processor, or may be formed of a plurality of processors. The controller 45 can store information or the like in the storage medium 46, and can read information or the like stored in the storage medium 46, via an interface such as a bus. Besides, the controller 45 detects whether an operation input is executed in the footswitch 11 that is the operation input section. Based on the operation input or the like in the footswitch 11, the controller 45 controls, via the interface such as a bus, the output of high-frequency electric energy (first electric energy) from the high-frequency driving circuit 42, and the output of heat generating electric energy (second electric energy) from the heat generating driving circuit 43. In addition, the output state of high-frequency electric energy from the high-frequency driving circuit 42 and the output state of heat generating electric energy from the heat generating driving circuit 43 are fed back to the controller 45 via the interface such as a bus.

One end of each of high-frequency electrical paths 47A and 47B is connected to the high-frequency driving circuit 42. The high-frequency electrical paths 47A and 47B extend through the inside of the cable 8 and the inside of the energy treatment instrument 2. The other end of the high-frequency electrical path 47A is connected to the blade (first electrode) 26 of the first clamp 16, and the other end of the high-frequency electrical path 47B is connected to the electrode member (second electrode) 36 of the second clamp 17. By the high-frequency electric energy being output from the high-frequency driving circuit (energy output section) 42, the high-frequency electric energy is supplied to the blade 26 through the high-frequency electrical path 47A, and the high-frequency electric energy is supplied to the electrode member 36 through the high-frequency electrical path 47B.

By the high-frequency electric energy (first electric energy) being supplied to the blade (first electrode) 26, the blade 26 has a first electric potential E1. By the high-frequency electric energy being supplied to the electrode member (second electrode) 36, the electrode member 36 has a second electric potential E2 which is different from the first electric potential E1. Accordingly, by the high-frequency electric energy being supplied to the blade 26 and electrode member 36, a high-frequency voltage V is applied between the blade 26 (high-frequency electrical path 47A) and the electrode member 36 (high-frequency electrical path 47B). By the high-frequency voltage V being applied between the blade 26 and the electrode member 36 in the state in which the treated target is grasped between the clamps 16 and 17, a high-frequency current I flows between the blade (first electrode) 26 and the electrode member (second electrode) 36 through the grasped treated target. The controller 45 adjusts the magnitudes of the high-frequency current I, high-frequency voltage V and high-frequency electric power P by controlling the output of the high-frequency electric energy.

The output state of the high-frequency electric energy from the high-frequency driving circuit 42 is fed back to the controller 45. Thus, in the state in which the high-frequency electric energy is being output, a variation with time of the high-frequency current I and a variation with time of the high-frequency voltage V are fed back to the controller 45. Based on the voltage value of the high-frequency voltage V and the current value of the high-frequency current I, the controller 45 detects, with the passing of time, a tissue impedance (high-frequency impedance) Z of the grasped treated target (biological tissue). Specifically, based on the high-frequency electric energy (first electric energy) that is output, the controller 45 detects the tissue impedance Z. In the present embodiment, the controller 45 judges, based on the tissue impedance Z, the dehydration state of moisture in the grasped treated target. In the meantime, when a phase difference φ between the high-frequency current I and high-frequency voltage V is defined, the tissue impedance Z is calculated in one example by the following equation (1).

$$Z = V/I \times \cos \varphi \tag{1}$$

One end of each of heat generating electrical paths 48A and 48B is connected to the heat generating driving circuit 43. The heat generating electrical paths 48A and 48B extend through the inside of the cable 8 and the inside of the energy treatment instrument 2, and the other ends thereof are connected to the heating body 27 of the first clamp 16. By the heat generating electric energy being output from the heat generating driving circuit (energy output section) 43, the heat generating electric energy is supplied to the heating body 27 through the heat generating electrical paths 48A and 48B. By the heat generating electric energy (second electric energy) being supplied to the heating body 27, a heat generating current I'A flows in the heating body 27, and the end effector 15 is actuated. At this time, a heat generating voltage V'A is applied between the heat generating electrical paths 48A and 48B. By the end effector 15 being actuated (by the heat generating current I'A flowing in the heating body 27), the heat generating electric energy is converted to heat in the heating body 27. Thereby, heat is generated in the heating body 27, and the generated heat is transmitted (conducted) to the grasping surface (first grasping surface) 21 of the first clamp 16 through the blade 26. In addition, the transmitted heat is applied from the grasping surface 21 to the grasped treated target. The controller 45 adjusts the magnitudes of the heat generating current I'A, heat generating voltage V'A and heat generating electric power P'A by controlling the output of the heat generating electric energy. By the magnitudes of the heat generating current I'A, heat generating voltage V'A and heat generating electric power P'A being adjusted, a calorific value Q'A of the heat generated in the heating body 27 is adjusted, and a temperature T of the grasping surface 21 (blade 26) is adjusted in the first clamp 16.

The output state of the heat generating electric energy from the heat generating driving circuit 43 is fed back to the controller 45. Thus, in the state in which the heat generating electric energy is being output, a variation with time of the heat generating current I'A and a variation with time of the heat generating voltage V'A are fed back to the controller 45. Based on the voltage value of the heat generating voltage V'A and the current value of the heat generating current I'A, the controller 45 detects, with the passing of time, a resistance value R of the heating body 27. Specifically, based on the heat generating electric energy that is output, the controller 45 detects the resistance value R of the heating body 27. For example, when the heat generating electric energy (second electric energy) is DC electric power, the resistance value R of the heating body 27 is calculated by the following equation (2).

$$R=V'A/I'A \qquad (2)$$

The resistance value R of the heating body 27 varies in accordance with the temperature of the heating body 27, that is, the temperature T of the grasping surface 21 (blade 26) to which heat is transmitted from the heating body 27. If the temperature T of the grasping surface (first grasping surface) 21 rises, the resistance value R of the heating body 27 increases. The storage medium 46 stores a table or the like, which indicates the relationship between the resistance value R of the heating body 27 and the temperature T of the grasping surface 21. In the state in which the heat generating electric energy is being output, the controller 45 detects the temperature T of the grasping surface 21 with the passing of time, by using the detected resistance value R, and the stored relationship between the resistance value R and the temperature T. In addition, based on the detected temperature T of the grasping surface 21 (the resistance value R of the heating body 27), the controller 45 adjusts the magnitudes of the heat generating current I'A, heat generating voltage V'A and heat generating electric power P'A, and adjusts the calorific value Q'A in the heating body 27.

Next, the function and advantageous effects of the energy treatment system 1 of the present embodiment will be described. When a treatment is performed by using the energy treatment system 1, a surgeon holds the housing 3 of the energy treatment instrument 2, and inserts the end effector 15 into a body cavity such as a peritoneal cavity. Then, a treated target is disposed between the grasping surface (first grasping surface) 21 of the first clamp 16 and the grasping surface (second grasping surface) 31 of the second clamp 17, and the handle 7 is closed relative to the grip 6. Thereby, the paired clamps 16 and 17 are closed relative to each other, and the treated target is grasped between the clamps 16 and 17. At this time, the grasping surface 21 of the first clamp 16 and the grasping surface 31 of the second clamp 17 are put in contact with the treated target. In the state in which the treated target is grasped between the clamps 16 and 17, the surgeon performs an operation input by the footswitch 11. Thereby, energy (high-frequency electric energy and heat generating electric energy) is supplied from the energy control device 10 to the energy treatment instrument 2.

Figure 5:
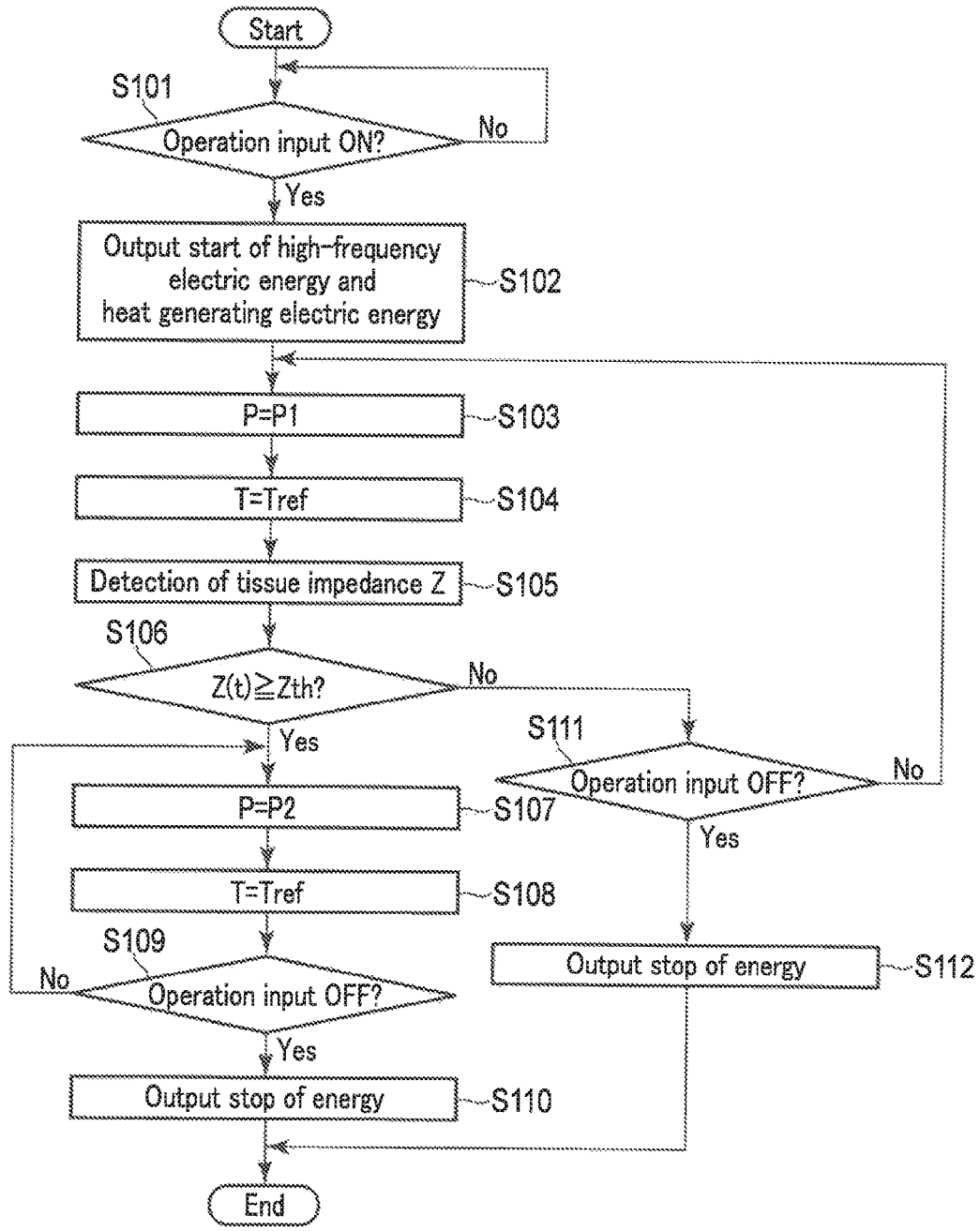
FIG. 5 is a flowchart illustrating a process in the energy control device in the supply of energy to the energy treatment instrument according to the first embodiment.

FIG. 5 is a flowchart illustrating a process in the energy control device 10 in the supply of energy from the energy control device 10 to the energy treatment instrument 2. As illustrated in FIG. 5, when energy is supplied to the energy treatment instrument 2 and the grasped treated target is treated, the controller 45 detects whether an operation input is performed in the footswitch 11 (step S101). Unless the operation input is detected (step 101—No), the process returns to step S101. If the operation input is detected (step S101—Yes), the controller 45 starts the output of high-frequency electric energy (high-frequency electric power P) from the high-frequency driving circuit (energy output section) 42, and starts the output of heat generating electric energy (heat generating electric power P'A) from the heat generating driving circuit (energy output section) 43 (step S102).

In the present embodiment, if the output of high-frequency electric energy (first electric energy) is started, the controller 45 controls the output of high-frequency electric energy by constant electric power control by which the high-frequency electric power P is kept constant with time at first electric power P1 (step S103). By the high-frequency electric energy being output, the high-frequency current I flows in the grasped treated target, and the treated target is denatured. Here, the first electric power P1 is low. Accordingly, in the state in which the high-frequency electric power P is kept constant with time at the first electric power P1, the high-frequency current I flowing in the grasped treated target is small, and the calorific value of the heat generated by the high-frequency current I is also small. Incidentally, the first electric power P1 is, for example, between 1 W and 15 W, and is, preferably, about 5 W.

In addition, in the present embodiment, if the output of heat generating electric energy (second electric energy) is started, the controller 45 controls the output of heat generating electric energy by constant temperature control by which the temperature T of the grasping surface (first grasping surface) 21 is kept constant with time at a reference temperature Tref (step S104). Specifically, the controller 45 adjusts the magnitudes of the heat generating current I'A, heat generating voltage V'A and heat generating electric power P'A, and adjusts the calorific value Q'A in the heating body 27, in such a state that the temperature T of the grasping surface 21 (blade 26) is kept constant with time at the reference temperature Tref. At this time, the controller 45 detects, with the passing of time, the resistance value R of the heating body 27 and the temperature T of the grasping surface 21, and executes feedback control. In addition, by keeping the resistance value R of the heating body 27 constant with time at a reference resistance value Rref, the controller 45 keeps the temperature T of the grasping surface 21 (the temperature of the heating body 27) constant with time at the reference temperature Tref. In the state in which the temperature T of the grasping surface 21 is constant with time at the reference temperature Tref, the grasped treated target is denatured by the heat generated by the heating body 27. Accordingly, by the constant temperature control, which keeps the temperature T of the grasping surface 21 constant with time at the reference temperature Tref, being continuously executed from the output start of heat generating electric energy, the heat generated by the heating body 27 continuously denatures the treated target from the output start of the heat generating electric energy (second electric energy). Incidentally, the reference temperature Tref is, for example, between 100° C. and 270° C., and is, preferably, about 200° C.

In addition, in the present embodiment, if the output of the high-frequency electric energy and heat generating electric energy is started, the controller 45 detects the tissue impedance Z with the passing of time (step S105). Time t, which is set with reference to the output start of (high-frequency electric energy and) heat generating electric energy, is defined as a variable. Upon detecting the tissue impedance Z, the controller 45 judges whether the tissue impedance Z(t) at time t is an impedance threshold value Zth or more (step S106). In this embodiment, the controller 45 judges, based on the tissue impedance Z(t), the dehydration state of moisture in the treated target from the output start of heat generating electric energy (in this embodiment, at the same time as the output start of high-frequency electric energy). Based on the judgment result of the dehydration state in the treated target, the controller 45 judges whether the treated target entered a predetermined state. Here, the predetermined state of the treated target is a state in which the treated target is denatured to some degree from the time of the output start of heat generating electric energy (second electric energy) by the heat generated by the heating body 27 (the heat generated by the actuation of the end effector 15), and is a state in which some degree of moisture in the treated target is dehydrated from the time of the output start of heat generating electric energy. The tissue impedance Z becomes higher as the moisture in the treated target becomes smaller. Accordingly, based on whether the tissue impedance Z(t) at time t is the impedance threshold value Zth or more, it is properly judged whether the treated target entered the predetermined state. Incidentally, the impedance threshold value Zth should preferably be greater than an initial impedance Z0 that is the tissue impedance Z (in the initial state) at the time of the output start of heat generating electric energy, and the impedance threshold value Zth is set in a range of, for example, between 50Ω and 500Ω.

If the tissue impedance Z(t) at time t is less than the impedance threshold value Zth (step S106—No), the controller 45 judges that the treated target is not in the predetermined state. Then, the controller 45 judges whether the operation input is continued by the footswitch 11 (step S111). If the operation input is stopped (step S111—Yes), the controller 45 stops the output of high-frequency electric energy from the high-frequency driving circuit 42 and the output of heat generating electric energy from the heat generating driving circuit 43 (step S112). If the operation input is continued (step S111—No), the process returns to step S103, and the above-described process of step S103 to S106 is continuously executed.

In step S106, if the tissue impedance Z(t) at time t is the impedance threshold value Zth or more (step S106—Yes), the controller 45 judges that the treated target entered the predetermined state. Then, the controller 45 controls the output of high-frequency electric energy by the constant electric power control which keeps the high-frequency electric power P constant with time at second electric power P2 (step S107). At this time, too, the high-frequency current I flows in the grasped treated target, and the treated target is denatured. Here, the second electric power P2 is greater than the first electric power P1. Accordingly, in the present embodiment, based on judging that the treated target entered the predetermined state in a state in which the heat generated by the heating body 27 is continuously denaturing the treated target, the controller 45 increases the high-frequency electric power P up to the second electric power P2 from the first electric power P1 before the time point at which it is judged that the treated target entered the predetermined state. In the state in which the high-frequency electric power P is kept constant with time at the second electric power P2 by being increased from the first electric power P1 to the second electric power P2, the high-frequency current I flowing in the grasped treated target is large, and also the calorific value Q of the heat generated by the high-frequency current I is large. Incidentally, the second electric power P2 is set in a range of, for example, between 15 W and 100 W.

In addition, in the present embodiment, even after the judgment that the treated target entered the predetermined state, the controller 45 controls the output of heat generating electric energy by the constant temperature control by which the temperature T of the grasping surface (first grasping surface) 21 is kept constant with time at the reference temperature Tref (step S108). Thus, even after the judgment that the treated target entered the predetermined state, the treated target is continuously denatured by the heat generated in the heating body 27.

Furthermore, in the state in which the constant electric power control (step S107) of high-frequency electric energy at the second electric power P2 and the constant temperature control (step S108) of heat generating electric energy at the reference temperature Tref are being executed, the controller 45 judges whether the operation input is continued by the footswitch (operation input section) 11 (step S109). If the operation input is stopped (step S109—Yes), the controller 45 stops the output of high-frequency electric energy and the output of heat generating electric energy (step S110). If the operation input is continued (step S110—No), the process returns to step S107, and the above-described process of step S107 to S109 is continuously executed.

As described above, in the present embodiment, the treated target is denatured by using the heat generated by the heating body 27 and the high-frequency current I flowing in the treated target. By the treated target being denatured by the high-frequency current I and the heat generated by the heating body 27, the treated target is coagulated and sealed. In addition, in this embodiment, since the output of high-frequency electric energy and heat generating electric energy is controlled as described above, the high-frequency electric energy (first electric energy) is continuously output at the same time as the heat generating electric energy (second electric energy), while the heat generated by the heating body 27 is continuously denaturing the treated target (while the heat generating electric energy is continuously output from the output start).

Figure 6C:
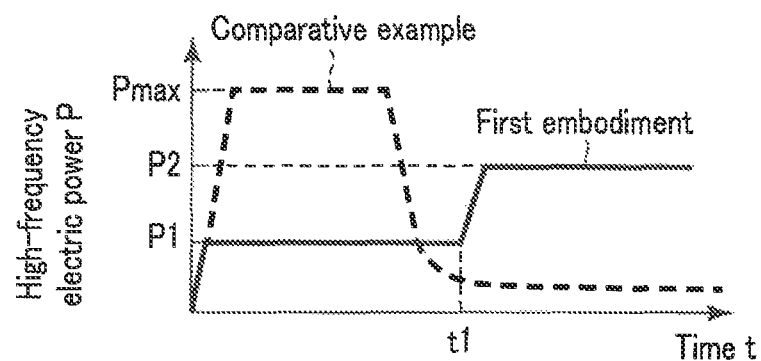
FIG. 6C is a schematic view illustrating an example of a variation with time of high-frequency electric power in a case in which the output of energy is controlled by the energy control device according to the first embodiment.
Figure 6D:
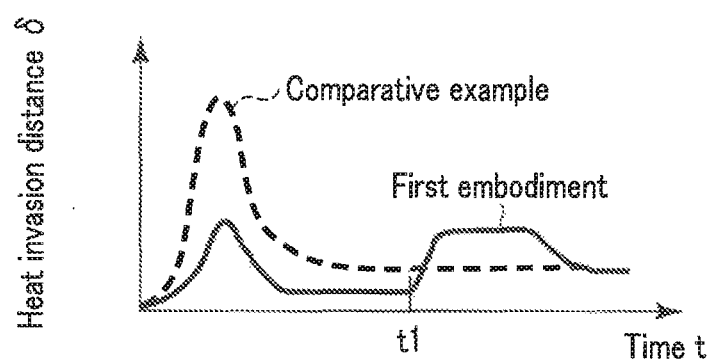
FIG. 6D is a schematic view illustrating an example of a variation with time of a heat invasion distance in a biological tissue in the width direction of the end effector, in a case in which the output of energy is controlled by the energy control device according to the first embodiment.

Here, in an example of the case in which the output of the energy (high-frequency electric energy and heat generating electric energy) is controlled by the energy control device 10 as described above, the temperature T of the grasping surface 21 (blade 26) varies with time, as illustrated in FIG. 6A; the tissue impedance Z varies with time, as illustrated in FIG. 6B; the high-frequency electric power P varies with time, as illustrated in FIG. 6C; and a heat invasion distance δ in a biological tissue including the treated target in the width direction of the end effector 15 varies with time, as illustrated in FIG. 6D. In FIG. 6A to FIG. 6D, the abscissa axis indicates time t which is set with reference to the output start of heat generating electric energy (in this embodiment, at the same time as the output start of high-frequency electric energy). In addition, in FIG. 6A, the ordinate axis indicates the temperature T. In FIG. 6B, the ordinate axis indicates the tissue impedance Z. In FIG. 6C, the ordinate axis indicates the high-frequency electric power P. In FIG. 6D, the ordinate axis indicates the heat invasion distance δ. In the state in which the high-frequency current I and the heat generated by the heating body 27 are denaturing the treated target, the heat generated by the high-frequency current I and the heat generated by the heating body 27 invade a part in the biological tissue, which is other than the treated target grasped between the clamps 16 and 17. Accordingly, in the biological tissue in the state in which the treated target is being denatured, the heat invades the part other than the treated target, from the treated target (the part grasped by the clamps 16 and 17), in the width direction of the end effector 15 (the direction of arrow B in FIG. 3). Here, in the biological tissue in the state in which the treated target is being denatured, a high-temperature range H, in which a tissue temperature T' is a boundary temperature T'0 or above, is defined. A distance from an edge of the end effector 15 to a boundary position of the high-temperature range H in the width direction of the end effector 15 is the heat invasion distance δ in the biological tissue.

As described above, in the present embodiment, in the state in which the heat generating electric energy (second electric energy) is being output, the constant temperature control is executed to keep the temperature T of the grasping surface (first grasping surface) 21 constant with time at the reference temperature Tref. Accordingly, as illustrated in FIG. 6A, if a certain length of time has passed since the output start of the heat generating electric energy, the temperature T of the grasping surface 21 rises to the reference temperature Tref. Then, after the temperature T of the grasping surface 21 rises to the reference temperature Tref, the temperature T of the grasping surface 21 is kept constant with time at the reference temperature Tref. In addition, in the present embodiment, at the same time as the output start of the heat generating electric energy, the output of the high-frequency electric energy is started. If the output of the high-frequency electric energy is started, the constant electric power control is executed to keep the high-frequency electric power P constant with time at the low first electric power P1. Accordingly, as illustrated in FIG. 6C, at the same time as the output start of the heat generating electric energy, the high-frequency electric energy with the first electric power P1 is output, and the high-frequency electric power P is kept constant with time at the low first electric power P1. By the output of heat generating electric energy and high-frequency electric power being started, the treated target is continuously denatured by the heat generated by the heating body 27, and the treated target is denatured by the high-frequency current I.

As illustrated in FIG. 6B, if the output of the heat generating electric energy and high-frequency electric energy is started, the tissue impedance Z decreases from an initial impedance Z0 (in the initial state) at the time of the output start of heat generating electric energy. Then, if the treated target is denatured to some degree from the time of the output start of heat generating electric energy (second electric energy) by the heat generated by the heating body 27 (the heat generated by the actuation of the end effector 15), and the moisture in the treated target is dehydrated to some degree from the time of the output start of heat generating electric energy, the treated target enters the above-described predetermined state. By the treated target entering the predetermined state (i.e. by the moisture in the treated target being dehydrated to some degree by denaturing from the time of the output start of heat generating electric energy), the tissue impedance Z transitions into a state of gradually increasing with the passing of time. In addition, even after the treated target entered the predetermined state (even after the tissue impedance Z begins to gradually increase with the passing of time), the treated target is continuously denatured by the heat generated by the heating body 27 and the high-frequency current I. Thereby, the tissue impedance Z increases over the impedance threshold value Zth. In FIG. 6B, at time t1, the tissue impedance Z increases up to the impedance threshold value Zth.

Accordingly, at time t1 or immediately thereafter, the controller 45 judges that the tissue impedance Z(t) increased to the impedance threshold value Zth or above, and that the treated target entered the predetermined state. Thus, as illustrated in FIG. 6C, at time t1 or immediately thereafter, the controller 45 increases the high-frequency electric power P from the first electric power P1 to second electric power P2. Then, after time t1, the high-frequency electric power P is kept constant with time at the high second electric power P2. In the meantime, as illustrated in FIG. 6A, even after time t1, the temperature T of the grasping surface 21 is kept constant with time at the reference temperature Tref.

Here, a comparative example will be illustrated, in which the control method of the output of high-frequency electric energy is different from the first embodiment. In the comparative example, like the first embodiment, the output of heat generating electric energy and the output of high-frequency electric energy are started at the same time, and the constant temperature control, which keeps the temperature T of the grasping surface 21 constant with time at the reference temperature Tref, is executed at the same time as the output start of the heat generating electric energy. However, in the comparative example, a high-frequency electric power P, which is substantially equal to the second electric power P2, or is greater than the second electric power P2, is output at the same time as the output start of the high-frequency electric energy. For example, during a length of time from the output start of high-frequency electric energy, constant electric power control is executed to keep the high-frequency electric power P constant with time at a maximum electric power Pmax, which is greater than the second electric power P2 and is a maximum value of the high-frequency electric power P within the outputtable range. In FIG. 6C and FIG. 6D, a variation with time in the first embodiment is indicated by a solid line, and a variation with time in the comparative example is indicated by a broken line.

Before the treated target is denatured by the high-frequency current I and the heat generated by heating body 27, the treated target contains some moisture. Thus, from when the denaturing of the treated target is started (from when the output of heat generating electric energy and high-frequency electric energy is started) to when the moisture in the treated target is dehydrated to some degree, the high-frequency current I tends to easily flow in a wide range in the width direction of the end effector 15 in the biological tissue including the grasped treated target. In addition, in the comparative example, at the same time as the output of heat generating electric energy and high-frequency electric energy is started, control is executed to keep the high-frequency electric power P constant with time at a large value (e.g. maximum electric power Pmax). In the state in which the high-frequency electric power P is kept at the large value, the high-frequency current I flowing in the grasped treated target is large, and also the calorific value Q of the heat generated by the high-frequency current I is large. Accordingly, in the comparative example, in the state in which the moisture of the treated target is not dehydrated immediately after the output start of heat generating electric energy and high-frequency electric energy, the large high-frequency current I flows in the wide range of the biological tissue including the treated target, and the heat of the large calorific value Q is generated by the high-frequency current I in the wide range of the biological tissue. Thus, in the biological tissue immediately after the output start, the high-temperature range H, in which the tissue temperature T' becomes the boundary temperature T'0 or above, becomes wider, and the heat invasion distance δ in the biological tissue, which is the distance from the edge of the end effector 15 to the boundary position of the high-temperature range H in the width direction of the end effector 15, becomes greater. Specifically, immediately after the output start, the invasion range of the heat (in particular, the heat generated by the high-frequency current I) increases in the biological tissue in the width direction of the end effector 15.

By contrast, in the present embodiment, immediately after the output start of heat generating electric energy and high-frequency electric energy, the control is executed to keep the high-frequency electric power P constant with time at the low first electric power P1. In the state in which the high-frequency electric power P is kept low, the high-frequency current I flowing in the grasped treated target is small, and also the calorific value Q of the heat generated by the high-frequency current I is small. Accordingly, in the state in which the moisture of the treated target is not dehydrated immediately after the output start, the high-frequency current I flows in the wide range of the biological tissue including the treated target, but the calorific value Q of the heat generated by the high-frequency current I is small. Thus, in the biological tissue immediately after the output start of heat generating electric energy and high-frequency electric energy, the high-temperature range H, in which the tissue temperature T' becomes the boundary temperature T'0 or above, becomes narrower, and the heat invasion distance δ in the biological tissue becomes smaller. Specifically, immediately after the output start, the invasion range of the heat (in particular, the heat generated by the high-frequency current I) decreases in the biological tissue in the width direction of the end effector 15.

Additionally, in the present embodiment, based on the judgment that the treated target entered the predetermined state, that is, based on the judgment that the moisture of the treated target was dehydrated to some degree from the output start, switching is effected to the constant electric power control to keep the high-frequency electric power P constant with time at the high second electric power P2. In the state in which the high-frequency electric power P is kept high, the high-frequency current I flowing in the grasped treated target is large, and also the calorific value Q of the heat generated by the high-frequency current I is large. However, in the present embodiment, the high-frequency electric power P is switched to the second electric power P2 in the state in which the moisture of the treated target was dehydrated to some degree from the output start. Thus, in the state in which the high-frequency electric power P that is set at the second electric power P2 is being output, the range in which the high-frequency current I flows becomes smaller in the biological tissue including the treated target. Since the range in which the high-frequency current I flows becomes smaller in the biological tissue, the heat generated by the high-frequency current I hardly invades the biological tissue, even if the calorific value Q by the high-frequency current I becomes large. Thus, in the biological tissue in the state in which the high-frequency electric power P that is set at the second electric power P2 is being output, the high-temperature range H, in which the tissue temperature T' becomes the boundary temperature T'0 or above, becomes smaller, and the heat invasion distance δ in the biological tissue becomes smaller. Specifically, even if the high-frequency electric power P, which is set at the second electric power P2, is output, the invasion range of the heat (in particular, the heat generated by the high-frequency current I) decreases in the biological tissue in the width direction of the end effector 15.

In the manner as described above, in the present embodiment, in the treatment of continuously denaturing the treated target by using the high-frequency current I and the heat generated by the heating body 27, it is possible to decrease the invasion range of the heat (the heat generated by the high-frequency current I and the heat generated by the heating body 27) in the biological tissue including the treated target. Specifically, in the present embodiment, while the treatment of denaturing the treated target is being performed, the heat invasion range in the biological tissue can continuously be kept small.

Additionally, in the present embodiment, the treated target is denatured by using the high-frequency current I flowing in the treated target, in addition to the heat generated by the heating body 27. By the high-frequency current I being used for the treatment, the coagulation performance and sealing performance in the treatment can be secured.

Additionally, in the present embodiment, while the heat generated by the heating body 27 is continuously denaturing the treated target (while the heat generating electric energy is being output continuously from the output start), the high-frequency electric energy (first electric energy) is continuously output at the same time as the heat generating electric energy (second electric energy). Thus, while the treatment of denaturing the treated target by the heat generated by the heating body 27 is being performed, the high-frequency current I is continuously applied to the treated target. Therefore, the coagulation performance and sealing performance in the treatment are improved.

(Second Embodiment)

Next, a second embodiment of the present invention will be described with reference to FIG. 7 to FIG. 8C. In the second embodiment, the configuration of the first embodiment is modified as described below. Incidentally, the same parts as in the first embodiment are denoted by like reference numerals, and a description thereof is omitted.

Figure 7:
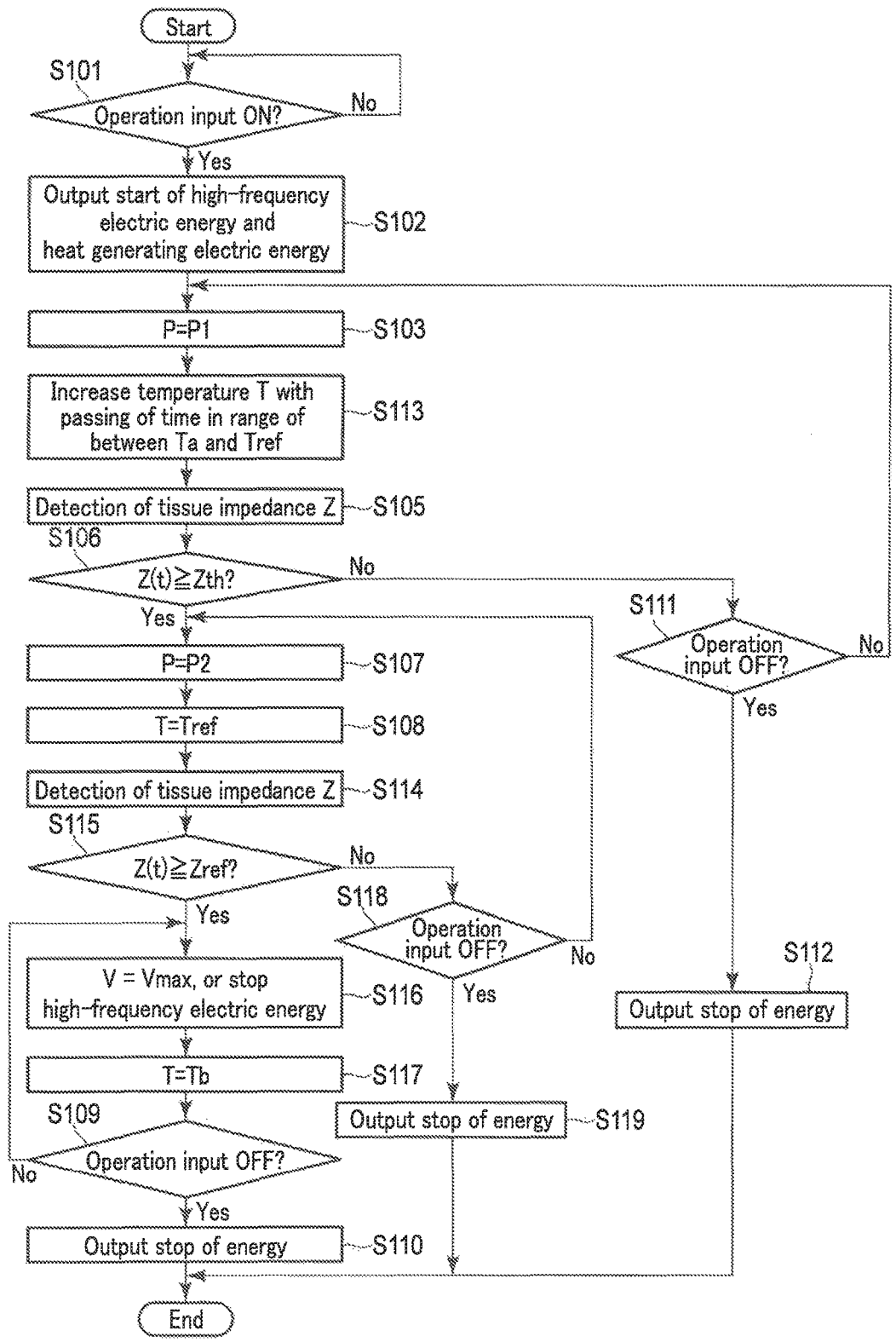
FIG. 7 is a flowchart illustrating a process in an energy control device in the supply of energy to an energy treatment instrument according to a second embodiment.

FIG. 7 is a flowchart illustrating a process in the energy control device 10 in the supply of energy from the energy control device 10 to the energy treatment instrument 2 in the present embodiment. As illustrated in FIG. 7, in this embodiment, like the first embodiment, when energy is supplied to the energy treatment instrument 2 and the grasped treated target is treated, the process of steps S101 and S102 is executed. Then, like the first embodiment, if the output of high-frequency electric energy (first electric energy) and heat generating electric energy (second electric energy) is started, the controller 45 controls the output of high-frequency electric energy by the constant electric power control by which the high-frequency electric power P is kept constant with time at the first electric power P1 (step S103). However, in the present embodiment, the process of step S104 is not executed. If the output of the heat generating electric energy (second electric energy) is started, the controller 45 controls the output of the heat generating electric energy in such a state that the temperature T of the grasping surface (first grasping surface) 21 increases with the passing of time in a range of between a temperature (initial temperature) Ta and a reference temperature Tref (step S113). Specifically, the heat generating current I'A, heat generating voltage V′A and heat generating electric power P′A are adjusted in such a state that the temperature T increases from the temperature (initial temperature) Ta with the passing of time in the range of not greater than the reference temperature Tref.

In addition, in the present embodiment, like the first embodiment, the process of steps S105, S106, S111 and S112 is executed. Thus, in this embodiment, as long as the tissue impedance Z(t) at time t is less than the impedance threshold value Zth (step S106—No) and the operation input is continued (step S111—No), the above-described process of step S103, S113, S105 and S106 is continuously executed. Accordingly, as long as it is judged that the tissue impedance Z(t) is less than the impedance threshold value Zth (i.e. as long as the treated target is not in the predetermined state), the temperature T of the grasping surface 21 increases with the passing of time in the range of between the temperature Ta and the reference temperature Tref, and is kept at the reference temperature Tref or less. Here, although the temperature Ta is less than the reference temperature Tref, the grasped treated target is denatured by the heat generated by the heating body 27 in the state in which the temperature T of the grasping surface 21 is increasing with time from the temperature (initial temperature) Ta. Accordingly, in this embodiment, too, by the control, which increases the temperature T of the grasping surface 21 with the passing of time in the range of between the temperature Ta and the reference temperature Tref, being continuously executed from the output start of heat generating electric energy, the heat generated by the heating body 27 continuously denatures the treated target from the output start of heat generating electric energy (second electric energy). Incidentally, the temperature Ta is, for example, between 60° C. and 270° C., and is, preferably, about 100° C.

If the tissue impedance Z(t) at time t is the impedance threshold value Zth or more (step S106—Yes), the controller 45, as in the first embodiment, controls the output of high-frequency electric energy by the constant electric power control by which the high-frequency electric power P is kept constant with time at the second electric power P2 (step S107), and controls the output of heat generating electric energy by the constant temperature control by which the temperature T of the grasping surface 21 is kept constant with time at the reference temperature Tref (step S108). However, in the present embodiment, even after it is judged that the tissue impedance Z(t) has increased to the impedance threshold value Zth or more, the controller 45 continuously detects the tissue impedance Z (step S114). Then, the controller 45 judges whether the tissue impedance Z(t) has increased to an impedance reference value Zref or more (step S115). The impedance reference value Zref is greater than the impedance threshold value Zth, and is set in a range of, for example, between 100Ω and 1000Ω.

If the tissue impedance Z(t) is less than the impedance reference value Zref (step S115—No), the controller 45 detects whether the operation input by the footswitch 11 is continued or not (step S118). If the operation input is stopped (step S118—Yes), the controller 45 stops the output of high-frequency electric energy and the output of heat generating electric energy (step S119). If the operation input is continued (step S118—No), the process returns to step S107, and the above-described process of step S107, S108, S114 and S115 is continuously executed.

In step S115, if the tissue impedance Z(t) is the impedance reference value Zref or more (step S115—Yes), the controller 45 controls the output of high-frequency electric energy, for example, by constant voltage control which keeps the high-frequency voltage V constant with time at a maximum voltage Vmax, which is a maximum value of the high-frequency voltage V in the outputtable range (S116). At this time, alternatively, the controller 45 may stop the output of high-frequency electric energy (step S116). In addition, based on the judgment that the tissue impedance Z(t) is the impedance reference value Zref or more (step S115—Yes), the controller 45 controls the output of heat generating electric energy by constant temperature control by which the temperature T of the grasping surface 21 is kept constant with time at a temperature (cut-and-open temperature) Tb (step S117). The temperature Tb is higher than the reference temperature Tref. By the temperature T of the grasping surface 21 being kept at the temperature Tb with the passing of time, the grasped treated target is cut and opened. Accordingly, after the judgment in step S115 that the tissue impedance Z(t) is the impedance reference value Zref or more, the constant temperature control is executed to keep the temperature T of the grasping surface 21 constant with time at the temperature (cut-and-open temperature) Tb, and thus the treated target is cut and opened by the heat generated by the heating body 27. Incidentally, the temperature Tb is, for example, between 200° C. and 400° C., and is, preferably, about 300° C.

In the present embodiment, in the state in which the constant temperature control of heat generating electric energy is being executed at the temperature (cut-and-open temperature) Tb, the controller 45 detects whether the operation input by the footswitch 11 is continued or not (step S109). If the operation input is stopped (step S109—Yes), the controller 45 stops the output of high-frequency electric energy and the output of heat generating electric energy (step S110). At this time, if the high-frequency electric energy is already stopped in step S116, the controller 45 keeps the stop of high-frequency electric energy, and stops the output of heat generating electric energy. In addition, if the operation input is continued (step S109—No), the process returns to step S116, and the above-described process of steps S116, S117 and S109 is continuously executed.

Figure 8A:
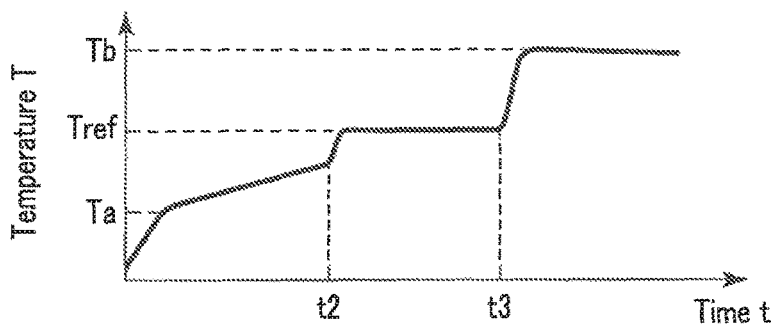
FIG. 8A is a schematic view illustrating an example of a variation with time of a temperature of a grasping surface in a case in which the output of energy is controlled by the energy control device according to the second embodiment.
Figure 8B:
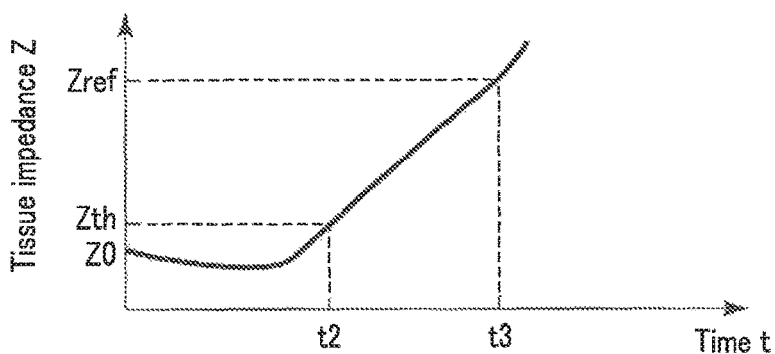
FIG. 8B is a schematic view illustrating an example of a variation with time of a tissue impedance in a case in which the output of energy is controlled by the energy control device according to the second embodiment.
Figure 8C:
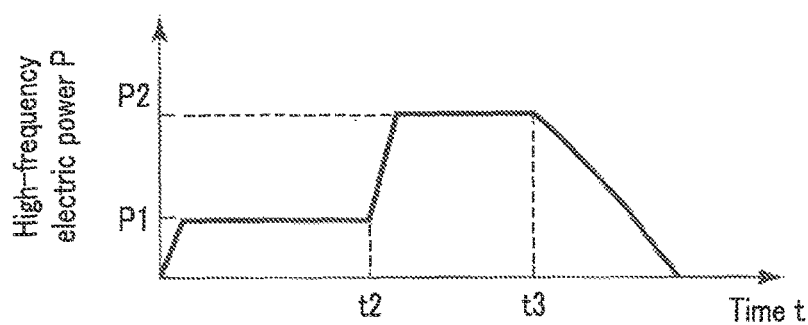
FIG. 8C is a schematic view illustrating an example of a variation with time of high-frequency electric power in a case in which the output of energy is controlled by the energy control device according to the second embodiment.

In an example of the case in which the output of the energy is controlled by the energy control device 10 of the present embodiment as described above, the temperature T of the grasping surface 21 (blade 26) varies with time, as illustrated in FIG. 8A; the tissue impedance Z varies with time, as illustrated in FIG. 8B; and the high-frequency electric power P varies with time, as illustrated in FIG. 8C. In FIG. 8A to FIG. 8C, the abscissa axis indicates time t which is set with reference to the output start of heat generating electric energy (in this embodiment, at the same time as the output start of high-frequency electric energy). In addition, in FIG. 8A, the ordinate axis indicates the temperature T. In FIG. 8B, the ordinate axis indicates the tissue impedance Z. In FIG. 8C, the ordinate axis indicates the high-frequency electric power P.

In the present embodiment, since the above-described control is executed, if a certain length of time has passed since the output start of the heat generating electric energy, as illustrated in FIG. 8A, the temperature T of the grasping surface 21 rises to the temperature Ta. Then, the temperature T of the grasping surface 21 increases with the passing of time in the range of between the temperature Ta and the reference temperature Tref. In addition, as illustrated in FIG. 8C, at the same time as the output start of the heat generating electric energy, the high-frequency electric energy is output with the first electric power P1, and the high-frequency electric power P is kept constant with time at the low first electric power P1. At this time, like the first embodiment, the treated target is continuously denatured by the heat generated by the heating body 27, and the treated target is denatured by the high-frequency current I.

By the heat generated by the heating body 27 (the heat generated by the actuation of the end effector 15), the treated target is denatured to some degree (the moisture in the treated target is dehydrated to some degree) from the time of the output start of heat generating electric energy (second electric energy). Thereby, the treated target enters the above-described predetermined state, and the tissue impedance Z transitions into a state of gradually increasing with the passing of time. As illustrated in FIG. 8B, by the tissue impedance Z gradually increasing with the passing of time, the tissue impedance Z at time t2 increases up to the impedance threshold value Zth. At time t2 or immediately thereafter, the controller 45 judges that the tissue impedance Z(t) has increased to the impedance threshold value Zth or more (the treated target entered the predetermined state). In addition, as illustrated in FIG. 8A, at time t2 or immediately thereafter, switching is effected to the constant temperature control to keep the temperature T of the grasping surface 21 constant with time at the reference temperature Tref. Besides, as illustrated in FIG. 8C, at time t2 or immediately thereafter, switching is effected to the constant electric power control to keep the high-frequency electric power P constant with time at the high second electric power P2. Even after the switching to the constant temperature control at the temperature Tref and to the constant electric power control at the second electric power P2, the treated target is continuously denatured by the heat generated by the heating body 27 and the high-frequency current I.

In addition, even after the tissue impedance Z(t) has increased to the impedance threshold value Zth, since the treated target is continuously denatured and the moisture in the treated target is dehydrated, the tissue impedance Z(t) continuously increases. Then, at time t3, the tissue impedance Z(t) increases to the impedance reference value Zref. At time t3 or immediately thereafter, the controller 45 judges that the tissue impedance Z(t) has increased to the impedance reference value Zref or more. In addition, as illustrated in FIG. 8A, at time t3 or immediately thereafter, switching is effected to the constant temperature control by which the temperature T of the grasping surface 21 is kept constant with time at the temperature Tb. After the switching to the constant temperature control at the temperature Tb, the treated target is cut and opened by the heat generated by the heating body 27. In addition, at time t3 or immediately thereafter, switching is effected to the constant voltage control which keeps the high-frequency voltage V constant with time at the maximum voltage Vmax. Even after the tissue impedance Z(t) has increased to the impedance reference value Zref, the tissue impedance Z(t) increases with the passing of time. Thus, as illustrated in FIG. 8C, after the switching to the constant voltage control at the maximum voltage Vmax, the high-frequency electric power P transitions into a state of decreasing from the second electric power P2 with the passing of time.

Also in the present embodiment, the high-frequency electric power P, which is set at the low first electric power P1, is output until the treated target enters the predetermined state (i.e. in the state in which the moisture of the treated target is not hydrated immediately after the output start of heat generating electric energy and high-frequency electric energy). Based on the fact that the treated target entered the predetermined state (the moisture in the treated target has been dehydrated to some degree), the high-frequency electric power P is increased to the high second electric power P2. Accordingly, also in the present embodiment, as described in the first embodiment, while the treatment of denaturing the treated target is being performed, the invasion range of the heat in the biological tissue (in particular, the heat generated by the high-frequency current I) can continuously be kept small. Furthermore, also in the present embodiment, since the treated target is denatured by using the high-frequency current I flowing in the treated target, in addition to the heat generated by the heating body 27, the coagulation performance and sealing performance in the treatment can be secured.

Additionally, in the present embodiment, until it is judged that the treated target entered the predetermined state (while the tissue impedance Z(t) is less than the impedance threshold value Zth), the output of heat generating electric energy is controlled in such a state that the temperature T of the grasping surface 21 increases with the passing of time from the temperature (initial temperature) Ta that is less than the reference temperature Tref. Since the above-described control is executed, the calorific value Q'A in the heating body 27 is small and the invasion range of the heat generated by the heating body 27 in the biological tissue including the treated target is small, before the judgment that the treated target entered the predetermined state. Thus, while the treatment of denaturing the treated target is being performed, the invasion range of the heat (the heat generated by the high-frequency current I and the heat generated by the heating body 27) in the biological tissue can further be decreased.

Additionally, in the present embodiment, based on the fact that the tissue impedance Z(t) has increased to the impedance reference value Zref or more, the control is executed to keep the temperature of the grasping surface 21 constant with time at the temperature Tb which is greater than the reference temperature Tref. Thus, the treatment of cutting and opening the treated target can be performed, in addition to the treatment of coagulating and sealing the treated target by denaturing the treated target.

(Modifications of the First Embodiment and Second Embodiment)

In the meantime, in the above-described embodiments, the controller 45 judges, based on the tissue impedance Z, whether the treated target entered the predetermined state (see steps S105 and S106 in FIG. 5 and FIG. 7). However, the restriction to this is unnecessary. FIG. 9 is a view illustrating patterns of judgment parameters and judgment conditions in judging whether the treated target entered the predetermined condition or not. In the above-described embodiments, whether the treated target entered the predetermined condition or not is judged by using the judgment parameter and judgment condition of a pattern X1. However, in one modification, whether the treated target entered the predetermined condition or not may be judged by using any one of patterns X2 to X12, in place of the pattern X1.

In the pattern X2, as the judgment parameters, use is made of a change rate ε of the tissue impedance (high-frequency impedance) Z and a count time Y. Here, the count time Y is a time which is counted by setting, as zero, a time point at which the change rate ε has changed to a positive value. In the pattern X2, the controller 45 detects the change rate ε of the tissue impedance Z with the passing of time, and starts counting the count time Y if the change rate ε has changed to a positive value. In addition, based on the fact that a change rate ε(t) at time t is positive and the count time Y is a reference count time Yref or more, the controller 45 judges that the tissue impedance Z has changed into a state of gradually increasing with time. Specifically, based on the fact that the positive state of the change rate ε has continued for the reference count time Yref, it is judged that the tissue impedance Z has changed into a state of gradually increasing with time. In addition, based on the judgment that the tissue impedance Z has changed into the state of gradually increasing with time, the controller 45 judges that the treated target entered the predetermined state. Besides, when the change rate ε goes back to zero or a negative value before the reference count time Yref has passed since the time point at which the change rate ε changed to the positive value, the controller 45 resets the count time Y to zero.

In the pattern X3, as the judgment parameter, use is made of a phase difference φ between the high-frequency current I and high-frequency voltage V. In this case, the controller 45 calculates a variation with time of the phase difference φ, from variations with time of the high-frequency current I and high-frequency voltage V. In addition, based on the fact that the absolute value of the difference between a phase difference φ(t) at time t and a phase difference φ(0) at the time of the output start of heat generating electric energy (the time of start of treatment) is a phase different threshold value φth or more, the controller 45 judges that the treated target entered the predetermined state. By the moisture in the treated target being dehydrated to some degree, the phase difference φ increases, compared to the time of the output start of high-frequency electric energy and heat generating electric energy. Accordingly, by using the phase difference φ as the criterion of judgment, it is properly judged whether the treated target entered the predetermined state (the state in which the moisture in the treated target is dehydrated to some degree from the time of the output start).

Additionally, as in the first embodiment, when the constant temperature control, which keeps the temperature T of the grasping surface 21 constant with time at the reference temperature Tref, is continuously executed from the output start of heat generating electric energy, it is possible to judge whether the treated target entered the predetermined state, by using any of the patterns X4 to X7.

In the pattern X4, a resistance value R of the heating body 27 is used as the judgment parameter. In this case, like the first embodiment, the controller 45 calculates the resistance value R with the passing of time, from the variations with time of the heat generating current I'A and heat generating voltage V'A. In addition, based on the fact that a resistance value R(t) at time t is a resistance threshold value Rth or more, the controller 45 judges that the treated target entered the predetermined state. Here, the resistance threshold value Rth is set to be equal to a reference resistance value Rref in a state in which the temperature of the grasping surface 21 is the reference temperature Tref, or set to be slightly less than the reference resistance value Rref. In the state in which the temperature T of the grasping surface 21 has risen to the reference temperature Tref by the heat generated by the heating body 27, the moisture in the treated target is dehydrated to some degree from the output start of heat generating electric energy. Accordingly, by using, as the judgment parameter, the resistance value R of the heating body 27 which varies in accordance with the temperature T of the grasping surface 21, it is properly judged whether the treated target entered the predetermined state.

In the pattern X5, as the judgment parameters, use is made of a change rate γ of the resistance value R of the heating body 27 and a count time U. Here, the count time U is a time which is counted by setting, as zero, a time point at which the absolute value of the change rate γ has changed to a change rate threshold value γth or less. In the pattern X5, the controller 45 detects the change rate γ of the resistance value R with the passing of time, and, if the absolute value of the change rate γ has changed to the change rate threshold value γth or less, starts counting the count time U. In addition, based on the fact that the absolute value of a change rate γ(t) at time t is the change rate threshold value γth or less and the count time U is a reference count time Uref or more, the controller 45 judges that the resistance value R has changed into a state of being constant with time. Specifically, based on the fact that the state in which the absolute value of the change rate γ is the change rate threshold value γth or less has continued for the reference count time Uref, it is judged that the resistance value R has changed into a state of being constant with time. In addition, based on the judgment that the resistance value R has changed into the state of being constant with time, the controller 45 judges that the treated target entered the predetermined state. Besides, when the absolute value of the change rate γ has become greater than the change rate threshold value γth once again before the reference count time Uref has passed since the time point at which the absolute value of the change rate γ changed to the change rate threshold value γth or less, the controller 45 resets the count time U to zero.

When the temperature T of the grasping surface 21 has changed into a state of being constant with time at the reference temperature Tref, the moisture in the treated target is dehydrated to some degree from the output start of heat generating electric energy. Accordingly, by using, as the judgment condition, the condition as to whether the resistance value R of the heating body 27, which varies in accordance with the temperature T of the grasping surface 21, has changed into the state of being constant with time at the reference resistance value Rref, it is properly judged whether the treated target entered the predetermined state.

Additionally, in the pattern X6, instead of using the resistance value R of the heating body 27 in the pattern X4, a temperature sensor (not shown) or the like directly detects the temperature T of the grasping surface 21, and the controller 45 judges whether the treated target entered the predetermined state, by using the detected temperature T. In addition, based on the fact that the temperature T(t) at time t is a temperature threshold value Tth or more, the controller 45 judges that the treated target entered the predetermined state.

Additionally, in the pattern X7, instead of using the change rate γ of the resistance value R and the count time U in the pattern X5, the temperature sensor or the like directly detects the temperature T of the grasping surface 21, and the controller 45 judges whether the treated target entered the predetermined state, by using a change rate γ' of the temperature T and a count time U'. In addition, based on the fact that the absolute value of a change rate γ'(t) at time t is a change rate threshold value γ'th or less and the count time U' is a reference count time U'ref or more, the controller 45 judges that the temperature T has changed into a state of being constant with time, and judges that the treated target entered the predetermined state. Specifically, based on the fact that the state in which the absolute value of the change rate γ' is the change rate threshold value γ'th or less has continued for the reference count time U'ref, it is judged that the treated target entered the predetermined state.

In the pattern X8, a water amount sensor (not shown) or the like detects a water content amount σ of the grasped treated target, and the controller 45 judges, based on the detected water content amount σ, whether the treated target entered the predetermined state. In addition, based on the fact that a water content amount σ(t) at time t is a water content amount threshold value σth or less, the controller 45 judges that the treated target entered the predetermined state. In the meantime, a laser sensor (not shown) may be provided in place of the water amount sensor, thereby detecting a transmittance of light in the treated target, or a frequency deviation of scattered light relative to incident light on the treated target, which occurs due to a Doppler effect. In this case, based on the transmittance or frequency deviation, the controller 45 detects the water content amount σ of the treated target and the flow of moisture in the treated target. In addition, based on the water content amount σ of the treated target and the flow of moisture in the treated target, the controller 45 judges whether the treated target entered the predetermined state.

In the pattern X9, an angle sensor (not shown) or the like detects an opening angle α between the paired clamps 16 and 17, and the controller 45 judges, based on the opening angle α, whether the treated target entered the predetermined state. In addition, based on the fact that an opening angle α(t) at time t is an angle threshold value αth or less, the controller 45 judges that the treated target entered the predetermined state. By the moisture in the treated target being dehydrated to some degree, the opening angle α becomes smaller than at the time of the output start of energy. Accordingly, by using the opening angle α as the judgment criterion, it is properly judged whether the treated target entered the predetermined state.

In the pattern X10, based on the time t which is set with reference to the output start of heat generating electric energy (second electric energy), the controller 45 judges the dehydration state of moisture in the treated target, and judges whether the treated target entered the predetermined state. In this case, based on the fact that the time t with reference to the output start has reached a change-over time ta or more, that is, based on the fact that the change-over time ta or more has passed since the output start of heat generating electric energy, the controller 45 judges that the treated target entered the predetermined state. In the pattern X10, the controller 45 calculates an interval time from the stop of the previous-time output of heat generating electric energy to the start of the present-time output of heat generating electric energy. In addition, based on the calculated interval time, the controller 45 determines the length of the change-over time ta.

Additionally, as indicated in the pattern X11, when the output of high-frequency electric energy and the output of heat generating electric energy are started at the same time, the controller 45 may judge whether the treated target entered the predetermined state, based on an integration value W of high-frequency electric power P from the output start of the high-frequency electric energy. In this case, based on the fact that an integration value W(t) at time t has reached an integration threshold value Wth or more, the controller 45 judges that the treated target entered the predetermined state. In the pattern X11, immediately before the output start of heat generating electric energy (high-frequency electric energy), the controller 45 detects the temperature T of the grasping surface 21 from the resistance value R of the heating body 27. In addition, the controller 45 determines the magnitude of the integration threshold value Wth, based on the temperature T of the grasping surface 21 immediately before the output start.

Additionally, as indicated in the pattern X12, whether or not the treated target entered the predetermined state may be judged by using, instead of the integration value W of high-frequency electric power P, an integration value W'A of the heat generating electric power P'A from the output start of heat generating electric energy. In this case, the controller 45 judges the treated target entered the predetermined state, based on the fact that an integration value W'A(t) at time t has reached an integration threshold value W'Ath or more.

Additionally, in one modification, the controller 45 can switch the output state of the high-frequency electric energy as described above, based on judging that the treated target entered the predetermined state, and the controller 45 can switch, based on the surgeon's operation of a button or the like, the output state of the high-frequency electric energy from the constant electric power control at the first electric power P1 to the constant electric power control at the second electric power P2. Thereby, when the surgeon judges that the treated target entered the predetermined state, the output state of high-frequency electric energy can be switched by the operation of the button or the like.

Additionally, in another modification, in the process of the second embodiment, which is illustrated in FIG. 7, the process of steps S114 to S119 may not be executed. In this case, the judgment of step S109 is executed in the state in which the constant electric power control of the high-frequency electric energy at the second electric power P2 (step S107) and the constant temperature control of the heat generating electric energy at the reference temperature Tref (step S108) are being executed.

In the meantime, in the above-described embodiments, based on the judgment that the treated target entered the predetermined state, the output of high-frequency electric power is switched from the constant electric power control at the first power P1 to the constant electric power control at the second power P2. However, the restriction to this is unnecessary. For example, in a first modification illustrated in FIG. 10A and FIG. 10B, if the output of high-frequency electric energy and heat generating electric energy is started, the controller 45 controls the output of the high-frequency electric energy by constant voltage control by which the high-frequency voltage V (the voltage value of the high-frequency voltage V) is kept constant with time at a first voltage V1, instead of the constant electric power control at the first electric power P1 (step S103). In addition, after the judgment that the treated target entered the predetermined state, the controller 45 controls the output of the high-frequency electric energy by constant voltage control by which the high-frequency voltage V (the voltage value of the high-frequency voltage V) is kept constant with time at a second voltage V2 that is higher than the first voltage V1, instead of the constant electric power control at the second electric power P2 (step S107).

Figure 10A:
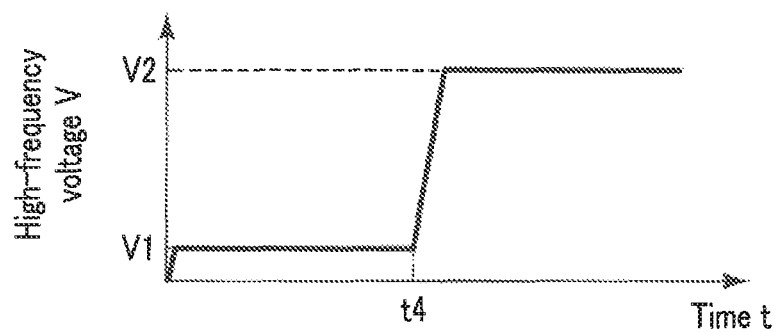
FIG. 10A is a schematic view illustrating an example of a variation with time of a high-frequency voltage in a case in which the output of energy is controlled by an energy control device according to a first modification of the first embodiment and second embodiment.
Figure 10B:
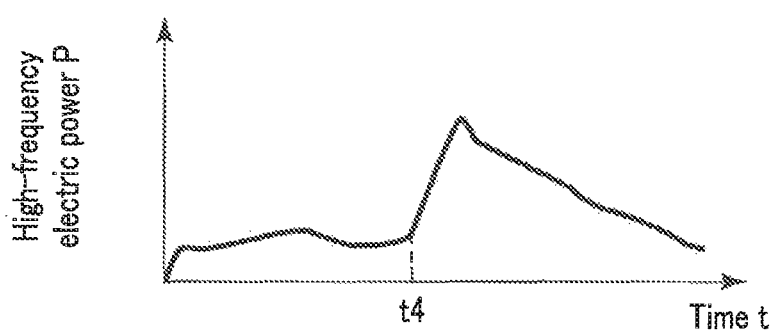
FIG. 10B is a schematic view illustrating an example of a variation with time of high-frequency electric power in a case in which the output of energy is controlled by the energy control device according to the first modification of the first embodiment and second embodiment.

Incidentally, as an example of the case in which the output of energy is controlled by the energy control device 10 of the present modification, the high-frequency voltage V varies with time, as illustrated in FIG. 10A, and the high-frequency electric power P varies with time, as illustrated in FIG. 10B. In FIG. 10A and FIG. 10B, the abscissa axis indicates time t which is set with reference to the output start of heat generating electric energy. In FIG. 10A, the ordinate axis indicates the high-frequency voltage V. In FIG. 10B, the ordinate axis indicates the high-frequency electric power P. In the present modification, too, for example, by using any one of the patterns X1 to X11, it is judged whether the treated target entered the predetermined state. In FIG. 10A and FIG. 10B, at time t4 or immediately thereafter, it is judged that the treated target entered the predetermined state (the state in which the moisture in the treated target is dehydrated to some degree), and at time t4 or immediately thereafter, the controller 45 increases the high-frequency voltage V from the first voltage V1 to the second voltage V2. By increasing the high-frequency voltage V, the high-frequency electric power P becomes higher than before the time point of the judgment that the treated target entered the predetermined state.

As described above, also in this modification, based on the judgment that the treat target entered the predetermined state, the controller 45 makes the high-frequency electric power P higher than before the time point of the judgment that the treated target entered the predetermined state. Incidentally, the tissue impedance Z increases with time, even after the switching to the constant voltage control at the second voltage V2 (even after the judgment that the treated target entered the predetermined state). Thus, as illustrated in FIG. 10B, after the switching to the constant voltage control at the second voltage V2, the high-frequency electric power P transitions into a state of decreasing with time.

Additionally, after the judgment that the treated target entered the predetermined state, the controller 45 may increase with time the high-frequency electric power P from the first electric power P1 in a manner of a linear function as in a second modification illustrated in FIG. 11A, or the controller 45 may increase with time the high-frequency electric power P from the first electric power P1 in a manner of a quadratic function as in a third modification illustrated in FIG. 11B. In each of these modifications, like the first embodiment, until it is judged that the treated target entered the predetermined state, the controller 45 controls the output of the high-frequency electric energy by the constant electric power control which keeps the high-frequency electric power P constant with time at the low first electric power P1. Accordingly, also in each of these modifications, based on judging that the treat target entered the predetermined state, the controller 45 makes the high-frequency electric power P higher than before the time point of the judgment that the treated target entered the predetermined state.

Additionally, as in a fourth modification illustrated in FIG. 11C, until the judgment that the treated target entered the predetermined state, only the heat generating electric energy may be output, and the high-frequency electric energy may not be output. In the present modification, based on the judgment that the treated target entered the predetermined state, the controller 45 starts the output of the high-frequency electric energy, and controls the output of the high-frequency electric energy by the constant electric power control which keeps the high-frequency electric power P constant with time at the high second electric power P2. Accordingly, based on the judgment that the treated target entered the predetermined state, the controller 45 increases the high-frequency electric power from zero to the second electric power P2. In addition, in the present modification, the high-frequency electric energy (first electric energy) is output at the same time as the heat generating electric energy (second electric energy), only in a part of a period during which the heat generated by the heating body 27 is continuously denaturing the treated target (a period during which the heat generating electric energy is output continuously from the output start) (only after the time point of the judgment that the treated target entered the predetermined state).

Incidentally, in FIG. 11A to FIG. 11C, the abscissa axis indicates time t which is set with reference to the output start of heat generating electric energy, and the ordinate axis indicates high-frequency electric power P. In addition, at time t5 or immediately thereafter in FIG. 11A, at time t6 or immediately thereafter in FIG. 11B, and at time t7 or immediately thereafter in FIG. 11C, it is judged that the treated target entered the predetermined state, and the controller 45 makes the high-frequency electric power P higher than before the time point of the judgment that the treated target entered the predetermined state.

(Third Embodiment)

Next, a third embodiment of the present embodiment will be described with reference to FIG. 12 to FIG. 14. In the third embodiment, the configuration of the first embodiment is modified as described below. Incidentally, the same parts as in the first embodiment are denoted by like reference numerals, and a description thereof is omitted.

In the present embodiment, the energy treatment instrument 2 (end effector 15) is not provided with the heating body 27. Instead, piezoelectric elements 51 (four piezoelectric elements in this embodiment), which are a vibration generator, are provided in the inside of the housing 3. Each of the piezoelectric elements 51 is sandwiched between ultrasonic electrodes 52A and 52B. The piezoelectric elements 51 and ultrasonic electrodes 52A and 52B are attached to a proximal portion of a vibration transmitting body 50. The vibration transmitting body 50 extends along the longitudinal axis C from the inside of the housing body 5 through the inside of the shaft 13 toward the distal side (arrow C1 side). In addition, a distal portion of the vibration transmitting body 50 projects from the distal side of the shaft 13, and the second clamp 17 is formed by a projecting portion of the vibration transmitting body 50. In the present embodiment, too, the first clamp 16 is rotatably attached to the distal portion of the shaft 13. In addition, by opening or closing the handle 7 relative to the grip 6, the clamps 16 and 17 open or close relative to each other.

In the present embodiment, the energy control device 10 includes an ultrasonic driving circuit 55 in place of the heat generating driving circuit 43. The ultrasonic driving circuit 55 includes a converter circuit which converts electric power from the electric power source 41 to vibration generating electric energy (ultrasonic electric energy). An output of vibration generating electric energy (second electric energy) from the ultrasonic driving circuit 55 is controlled by the controller 45 via an interface such as a bus. In addition, the output state of the vibration generating electric energy from the ultrasonic driving circuit 55 is fed back to the controller 45 via the interface such as a bus. In this embodiment, in place of the footswitch 11, an operation button 57 is attached to the housing 3 as the operation input section. In addition, a switch 58 is provided in the inside of the housing 3. The open or closed state of the switch 58 changes based on the presence or absence of the operation input by the operation button 57. Accordingly, the controller 45 detects whether the operation input is executed by the operation button 57, by detecting the open or closed state of the switch 58.

Also in the present embodiment, the high-frequency electric energy (first electric energy), which is output from the high-frequency driving circuit 42, is supplied to the first clamp 16 through the high-frequency electrical path 47A, and is supplied to the second clamp 17 through the high-frequency electrical path 47B. Thereby, the high-frequency voltage V is applied between the clamps (electrodes) 16 and 17, and the high-frequency current I flows between the first clamp (first electrode) 16 and the second clamp (second electrode) 17 through the grasped treated target. Thus, like the above-described embodiments, etc., the treated target is denatured by the high-frequency current I. In addition, the controller 45 controls the output of the high-frequency electric energy from the high-frequency driving circuit 42, in the same manner as in the first embodiment.

One end of each of vibration generating electric paths 56A and 56B is connected to the ultrasonic driving circuit 55. The vibration generating electrical paths 56A and 56B extend through the inside of the cable 8. In addition, the other end of the vibration generating electrical path 56A is connected to the ultrasonic electrode (first ultrasonic electrode) 52A, and the other end of the vibration generating electrical path 56B is connected to the ultrasonic electrode (second ultrasonic electrode) 52B. By the vibration generating electric energy being output from the ultrasonic driving circuit (energy output section) 55, the vibration generating electric energy (second electric energy) is supplied to the piezoelectric elements (vibration generator) 51 through the vibration generating electrical paths 56A and 56B. Thereby, a vibration generating voltage V'B is applied between the ultrasonic electrodes 52A and 52B, and a vibration generating current I'B flows through the piezoelectric elements 51.

By the vibration generating current I'B flowing through the piezoelectric elements 51, the vibration generating current I'B is converted to ultrasonic vibration, and ultrasonic vibration is generated. The ultrasonic vibration generated by the piezoelectric elements 51 is transmitted toward the second clamp 17 from the proximal side to distal side in the vibration transmitting body 50. By the ultrasonic vibration being transmitted to the second clamp 17, the end effector 15 is actuated. In the state in which the vibration transmitting body 50 is transmitting the ultrasonic vibration, the vibration transmitting body 50 including the second clamp 17 vibrates in a predetermined frequency range. At this time, an amplitude v and a vibration velocity in the second clamp 17 (vibration transmitting body 50) vary in accordance with the vibration generating current I'B (the current value of vibration generating current I'B). If the vibration generating current I'B increases, the amplitude v and vibration velocity in the second clamp 17 increase. By the second clamp 17 vibrating, frictional heat occurs between the second clamp 17 and the grasped treated target, and the treated target is treated by the frictional heat. A calorific value Q'B of the frictional heat by vibration increases as the amplitude v and vibration velocity in the second clamp 17 become greater. In the present embodiment, the controller 45 adjusts the magnitudes of the vibration generating current I'B, vibration generating voltage V'B and vibration generating electric power P'B by controlling the output of the vibration generating electric energy. By the vibration generating current I'B being adjusted, the amplitude v and vibration velocity in the second clamp 17 are adjusted and the calorific value Q'B of the frictional heat is adjusted.

Figure 13:
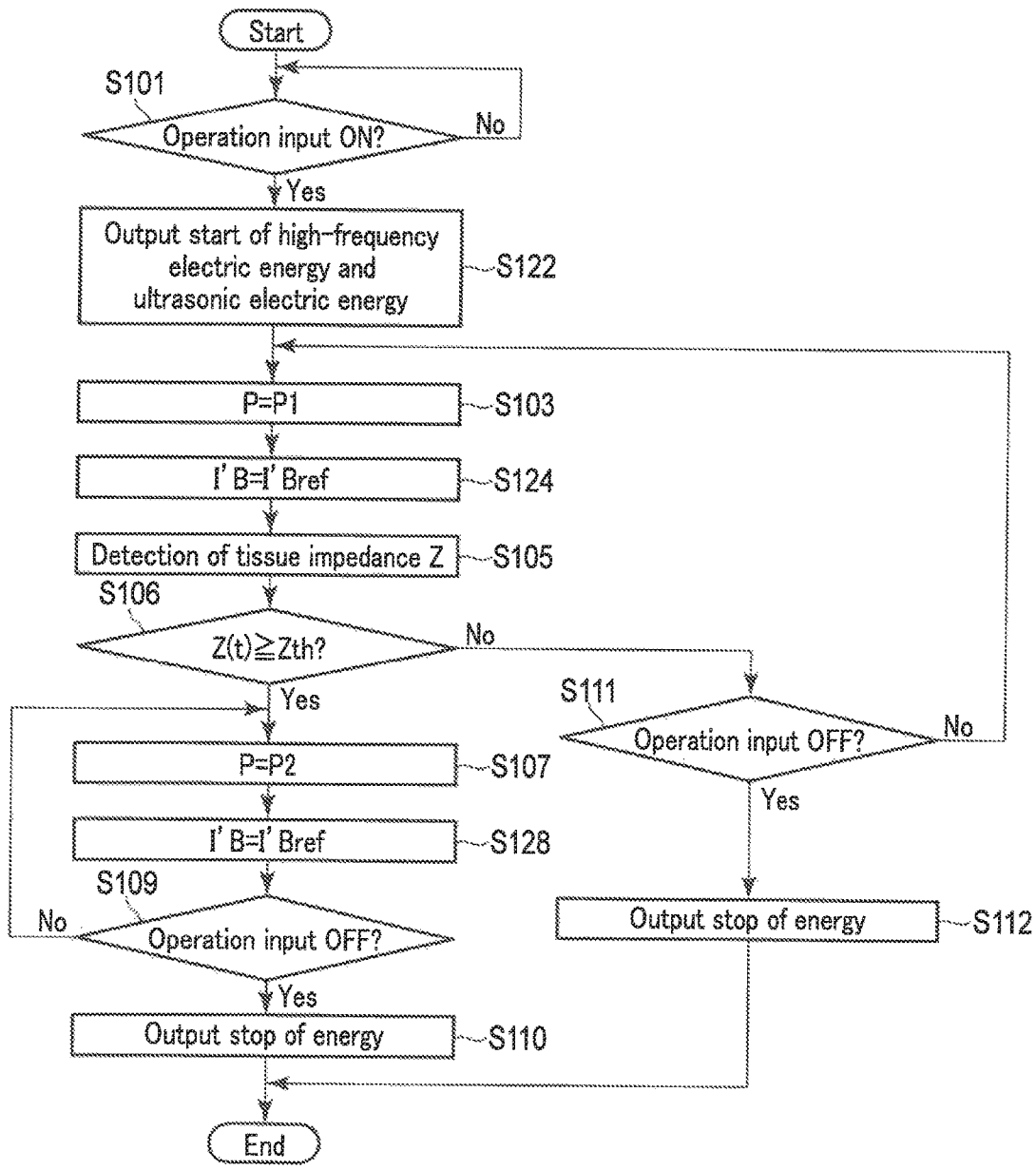
FIG. 13 is a flowchart illustrating a process in the energy control device in the supply of energy to an energy treatment instrument according to the third embodiment.

FIG. 13 is a flowchart illustrating a process in the energy control device 10 in the supply of energy from the energy control device 10 of the present embodiment to the energy treatment instrument 2. As illustrated in FIG. 13, also in this embodiment, like the above-described flow of FIG. 5, the process of steps S101, S103, S105 to S107, and S109 to S112 is executed. However, in the present embodiment, if the operation input by the operation button 57 is detected (step S101—Yes), the controller 45 starts the output of high-frequency electric energy and the output of vibration generating electric energy at the same time (step S122). In addition, if the output of vibration generating electric energy is started, the controller 45 controls the output of vibration generating electric energy by constant current control which keeps the vibration generating current I'B constant with time at a reference current value I'Bref (step S124). By the vibration generating current I'B being kept constant with time at the reference current value I'Bref, the second clamp 17 vibrates with the amplitude v that is kept constant with time at a reference amplitude vref. By the second clamp 17 vibrating continuously with the reference amplitude vref, frictional heat due to ultrasonic vibration occurs with such a large calorific value Q'B as to denature the grasped treated target. Accordingly, in the present embodiment, by the constant current control, which keeps the vibration generating current I'B constant with time at the reference current value I'Bref, being continuously executed from the output start of vibration generating electric energy, the frictional heat generated by the ultrasonic vibration continuously denatures the treated target from the output start of the vibration generating electric energy (second electric energy).

Additionally, also in this embodiment, like the first embodiment, the process of steps S103, and S105 to S107 is executed. Thus, based on the judgment that the treated target entered the predetermined state (in the present embodiment, based on the fact that the high-frequency impedance Z(t) is the impedance threshold value Zth or more), the controller 45 switches the output of the high-frequency electric energy from the constant electric power control at the low first electric power P1 (step S103) to the constant electric power control at the high second electric power P2 (step S107). In addition, even after the judgment that the treated target entered the predetermined state (the state in which the moisture in the treated target is dehydrated to some degree), the controller 45 continues the constant current control which keeps the vibration generating current I'B constant with time at the reference current value I'Bref (step S128).

Figure 14:
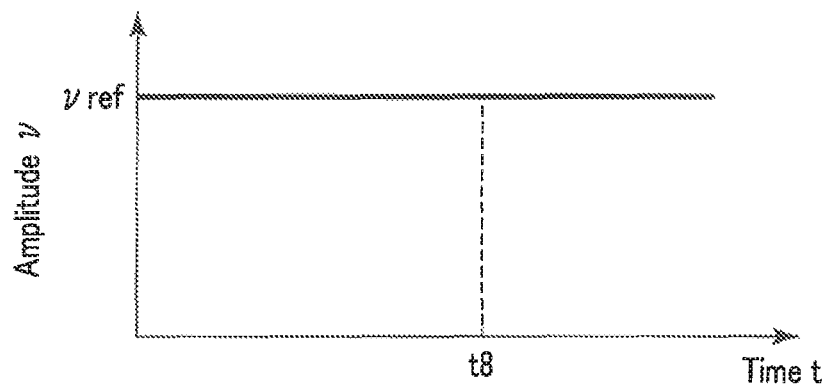
FIG. 14 is a schematic view illustrating an example of a variation with time of an amplitude in a second clamp in a case in which the output of energy is controlled by an energy control device according to the third embodiment.

As an example of the case in which the output of energy is controlled by the energy control device 10 of the present embodiment, the amplitude v in the second clamp 17 varies with time, as illustrated in FIG. 14. In FIG. 14, the abscissa axis indicates time t which is set with reference to the output start of vibration generating electric energy (the output start of high-frequency electric energy), and the ordinate axis indicates the amplitude v. In addition, in FIG. 14, at time t8 or immediately thereafter, it is judged that the treated target entered the predetermined state, and the controller 45 increases the high-frequency electric power P from the first electric power P1 to the second electric power P2. In the present embodiment, if the output of vibration generating electric energy is started, the controller 45 continuously executes the constant current control which keeps the vibration generating current I'B constant with time at the reference current value I'Bref. Accordingly, as illustrated in FIG. 14, if the output of vibration generating electric energy is started, the second clamp 17 continuously vibrates with the reference amplitude vref with the passing of time.

As described above, also in the present embodiment, the high-frequency electric power P, which is set at the low first electric power P1, is output until the treated target enters the predetermined state (i.e. in the state in which the moisture of the treated target is not hydrated immediately after the output start of vibration generating electric energy and high-frequency electric energy). Based on the fact that the treated target entered the predetermined state (the moisture in the treated target is dehydrated to some degree), the high-frequency electric power P is increased to the high second electric power P2. Accordingly, also in the present embodiment, as described in the first embodiment, while the treatment of denaturing the treated target is being performed, the invasion range of the heat in the biological tissue (in particular, the heat generated by the high-frequency current I) can continuously be kept small. Furthermore, in the present embodiment, since the treated target is denatured by using the high-frequency current I flowing in the treated target, in addition to the frictional heat generated by the ultrasonic vibration, the coagulation performance and sealing performance in the treatment can be secured.

(Modification of the Third Embodiment)

Figure 15:
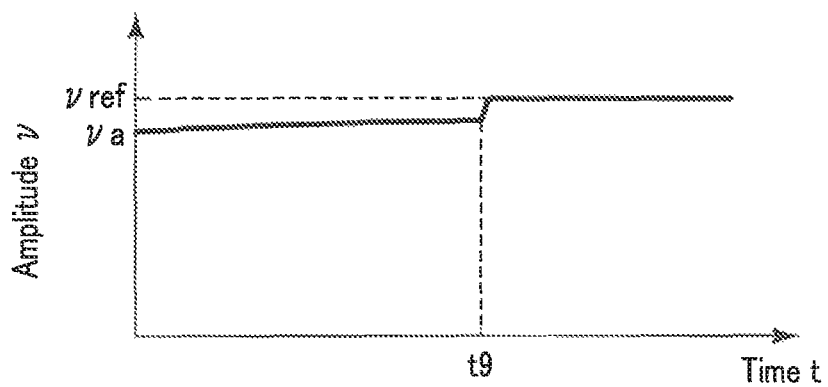
FIG. 15 is a schematic view illustrating an example of a variation with time of an amplitude in a second clamp in a case in which the output of energy is controlled by an energy control device according to a modification of the third embodiment.

In the meantime, in one modification of the third embodiment, which is illustrated in FIG. 15, until it is judged that the treated target entered the predetermined state, the controller 45 controls the output of the vibration generating electric energy in such a state that the vibration generating current I'B increases with time in a range between a current value (initial current value) I'Ba and the reference current value I'Bref. Thus, in the present modification, if the output of vibration generating current is started, the vibration generating current I'B increases with time from the current value I'Ba within the range of not greater than the reference current value I'Bref, and the amplitude v in the second clamp 17 increases with time from an amplitude (initial amplitude) va within the range of not greater than the reference amplitude vref. Here, the amplitude va is less than the reference amplitude vref. However, in the state in which the amplitude v in the second clamp 17 increases with time from the amplitude (initial amplitude) va, the calorific value Q'B of frictional heat by ultrasonic vibration is large to such a degree as to denature the treated target. Thus, also in the present modification, the control, which increases with time the amplitude v in the second clamp 17 within the range of between the amplitude va and the reference amplitude vref, is continuously executed from the output start of vibration generating electric energy. Thereby, the frictional heat generated by the ultrasonic vibration continuously denatures the treated target from the output start of the vibration generating electric energy (second electric energy).

In the present modification, based on judging that the treated target entered the predetermined state, the controller 45 executes switching to the constant current control which keeps the vibration generating current I'B constant with time at the reference current value I'Bref, and the second clamp 17 continuously vibrates with the reference amplitude vref. In the meantime, when the output of energy is controlled by the energy control device 10 of this modification, the amplitude v in the second clamp 17 changes with time, as illustrated in FIG. 15. In FIG. 15, the abscissa axis indicates time t which is set with reference to the output start of vibration generating electric energy, and the ordinate axis indicates the amplitude v. In addition, in FIG. 15, at time t9 or immediately thereafter, it is judged that the treated target entered the predetermined state, and the controller 45 increases the high-frequency electric power P from the first electric power P1 to the second electric power P2.

Incidentally, also in the case in which the vibration generating electric energy, in place of the heat generating electric energy, is output from the energy control device 10 as in the third embodiment, the judgment as to whether the treated target entered the predetermined state may be executed by using any one of the patterns (X1 to X12) described in FIG. 9. However, since the heat generating electric energy is not output, the judgment is executed by using any one of the patterns (any one of X1 to X3, and X8 to X11) excluding the patterns X4 to X7, and X12.

Additionally, also in the case in which the vibration generating electric energy, in place of the heat generating electric energy, is output from the energy control device 10 as in the third embodiment, the controller 45 may switch the output state of high-frequency electric energy, based on the judgment that the treated target entered the predetermined state, as described in modifications of the first embodiment and second embodiment (for example, as illustrated in any one of the modification of FIG. 10A and FIG. 10B, the modification of FIG. 11A, the modification of FIG. 11B and the modification of FIG. 11C).

(Other Modifications)

In the above-described embodiments, etc., the end effector (15) includes a pair of clamps (16, 17) which are openable and closable relative to each other. The end effector (15) is configured to be capable of grasping a treated target between the clamps (16, 17), and each of the clamps (16, 17) includes a corresponding electrode (corresponding one of 26 and 36; corresponding one of 16 and 17). The energy output section (42, 43; 42, 55) is configured to be capable of outputting first electric energy and second electric energy. By the first electric energy being supplied to the electrodes of the end effector (15), a high-frequency current (I) flows between the electrodes (26, 36; 16, 17) through the treated target grasped between the clamps (16, 17). By the second electric energy being output, the end effector (15) is actuated, and heat for use in a treatment of the treated target occurs in the end effector (15). The controller (45) is configured to control outputs of the first electric energy and the second electric energy from the energy output section (42, 43; 42, 55), and configured to continuously output the second electric energy from the energy output section (43; 55) in such a state that the treated target is continuously denatured from an output start of the second electric energy by the heat generated by the actuation of the end effector (15). In addition, the first electric energy is output from the energy output section (42, 43; 42, 55) at the same time as the second electric energy, in at least a part of a period during which the heat generated by the output of the second electric energy is continuously denaturing the treated target. In the state in which the heat is continuously denaturing the treated target, the controller (45) makes, based on judging that the treated target entered the predetermined state, the electric power (P) of the first electric energy greater than before a time point of the judgment that the treated target entered the predetermined state.

Additional advantages and modifications will readily occur to those skilled in the art. Therefore, the invention in its broader aspects is not limited to the specific details and representative embodiments shown and described herein. Accordingly, various modifications may be made without departing from the spirit or scope of the general inventive concept as defined by the appended claims and their equivalents.

What is claimed is:

1. An energy treatment system comprising:
    an end effector that includes a pair of clamps that are openable and closable relative to each other, the end effector being configured to grasp a treated target between the clamps;
    a pair of electrodes that is provided in the end effector, first electric energy being supplied to the electrodes so as to pass a high-frequency current between the electrodes and through the treated target that is grasped between the clamps;
    an electric element that is connected to the end effector, second electric energy being supplied to the electric element to actuate the end effector by generating heat in the end effector; and
    a controller that is configured to:
        output the second electric energy to the electric element from a first time point so as to denature, from the first time point, the treated target by the heat generated by the actuation of the end effector, judge whether or not the treated target entered a predetermined state after the first time point, the judgment being based on a dehydration state of the treated target, and execute one of:
(i) starting an output of the first electric energy to the electrodes at a second time point, which is at the same time as or after the first time point, and then increasing the output of the first electric energy after the second point based on judging that the treated target entered the predetermined state, and
(ii) starting an output of the first electric energy to the electrodes after the first time point based on judging that the treated target entered the predetermined state.

2. The energy treatment system of claim 1, wherein, when the output of the first electric energy is started at the second time point, the controller is further configured to:
detect a tissue impedance of the treated target after the second time point based on the output of the first electric energy,
judge the dehydration state of the treated target based on the tissue impedance, and
judge that the treated target entered the predetermined state after the second time point based on a determination that the tissue impedance reached an impedance threshold value or more or a determination that the tissue impedance changed into a state of gradually increasing with time.

3. The energy treatment system of claim 1, wherein the controller is further configured to:
detect the dehydration state of the treated target based on a time with reference to the first time point, and
judge that the treated target entered the predetermined state based on a determination that a change-over time or more has passed since the first time point.

4. The energy treatment system of claim 1, wherein:
the electric element includes a heating body that is provided in the end effector, the heating body being configured to convert the second electric energy to the heat by being supplied with the second electric energy, and
the controller is further configured to:
detect a resistance value of the heating body after the first time point on the output of the second electric energy,
judge the dehydration state of the treated target based on the resistance value, and
judge that the treated target entered the predetermined state after the first time point based on a determination that the resistance value reached a resistance threshold value or more or a determination that the resistance value changed into a state of being constant with time.

5. The energy treatment system of claim 1, wherein:
the pair of clamps includes a first clamp and a second clamp,
each of the first clamp and the second clamp includes a grasping surface that is configured to contact the treated target that is grasped, and includes a back surface that faces a side opposite to the grasping surface,
at least a part of the grasping surface of the first clamp is formed by the electrode, and
the first clamp includes a heating body as the electric element, the heating body being provided on a back surface side of the first clamp with respect to the electrode, the heating body being configured to convert the second electric energy to the heat by being supplied with the second electric energy, and being configured to transmit the generated heat to the grasping surface through the electrode.

6. The energy treatment system of claim 5, wherein the electrode of the first clamp includes a ridge portion that extends from a proximal portion to a distal portion of the first clamp on the grasping surface, the ridge portion being configured to be abuttable on the grasping surface of the second clamp, in a state in which the pair of clamps are closed relative to each other.

7. The energy treatment system of claim 1, wherein:
the electric element incudes a heating body that is provided in the end effector, the heating body being configured to convert the second electric energy to the heat by being supplied with the second electric energy, and
the controller is further configured to output the second electric energy to the heating body from the first time point by constant temperature control by which a temperature of the end effector is kept constant with time at a reference temperature, the treated target being denatured at the reference temperature.

8. The energy treatment system of claim 1, wherein:
the electric element includes a heating body that is provided in the end effector, the heating body being configured to convert the second electric energy to the heat by being supplied with the second electric energy, and
the controller is further configured to output the second electric energy to the heating body in a period ranging from a third time point, before the first time point, to the first time point by control by which a temperature of the end effector is increasing with time in a range that is an initial temperature or higher and a reference temperature of lower, the treated target being denatured at the reference temperature.

9. An energy control device configured to control a supply of energy to an energy treatment instrument, the energy treatment instrument being provided with an end effector including a pair of clamps that are openable and closable relative to each other, the end effector being configured to grasp a treated target between the clamps, the end effector including a pair of electrodes such that first electric energy is supplied to the electrodes so as to pass a high-frequency current between the electrodes and through the treated target that is grasped between the clamps, the energy treatment instrument including an electric element such that second electric energy is supplied to the electric element to actuate the end effector by generating heat in the end effector, the energy control device comprising:
a controller that is configured to:
output the second electric energy to the electric element from a first time point so as to denature, from the first time point, the treated target by the heat generated by the actuation of the end effector,
judge whether or not the treated target entered a predetermined state after the first time point, the judgment being based on a dehydration state of the treated target, and
execute one of:
(i) starting an output of the first electric energy to the electrodes at a second time point, which is at the same time as or after the first time point, and then increasing the output of the first electric energy after the second time point based on judging that the treated target entered the predetermined state, and (ii) starting an output of the first electric energy to the electrodes after the first time point based on judging that the treated target entered the predetermined state.

10. The energy control device of claim 9, wherein, when the output of the first electric energy is started at the second time point, the controller is further configured to:
   detect a tissue impedance of the treated target after the second time point based on the output of the first electric energy,
   judge the dehydration state of the treated target based on the tissue impedance, and
   judge that the treated target entered the predetermined state after the second time point based on a determination that the tissue impedance reached an impedance threshold value or more or a determination that the tissue impedance changed into a state of gradually increasing with time.

11. The energy control device of claim 9, wherein the controller is further configured to:
   detect the dehydration state of the treated target based on a time with reference to the first time point, and
   judge that the treated target entered the predetermined state based on a determination that a change-over time or more has passed since the first time point.

12. The energy control device of claim 9, wherein:
   the electric element includes a heating body that is provided in the end effector, the heating body being configured to convert the second electric energy to the heat by being supplied with the second electric energy, and
   the controller is further configured to:
      detect a resistance value of the heating body after the first time point based on the output of the second electric energy,
      judge the dehydration state of the treated target based on the resistance value, and
      judge that the treated target entered the predetermined state after the first time point based on a determination that the resistance value reached a resistance threshold value or more or a determination that the resistance value changed into a state of being constant with time.

13. An energy treatment instrument that is supplied with energy and that is used with an energy control device, the energy control device including a controller configured to control output of first electric energy and second electric energy,
   the energy treatment instrument comprising:
      an end effector that includes a pair of clamps that are openable and closable relative to each other, the end effector being configured to grasp a treated target between the clamps,
      a pair of electrodes that are provided in the end effector, the first electric energy being supplied to the electrodes so as to pass a high-frequency current between the electrodes and through the treated target that is grasped between the clamps, and
      an electric element that is connected to the end effector, the second electric energy being supplied to the electric element to actuate the end effector by generating heat in the end effector, wherein:
   by the second electric energy being output to the electric element, from a first time point, the treated target is denatured, from the first time point, by the heat generated by the actuation of the end effector,
   the output of the second electric energy is continued from the first time point while the controller judges whether or not the treated target entered a predetermined state, the judgment being based on a dehydration state of the treated target, and
   one of the following is satisfied:
      (i) output of the first electric energy to the electrodes is started at a second time point, which is at the same time as or after the first time point, and then, output of the first electric energy to the electrodes is increased after the second time point based on the controller judging that the treated target entered the predetermined state, and
      (ii) output of the first electric energy to the electrodes is started after the first time point based on the controller judging that the treated target entered the predetermined state.

14. The energy treatment instrument of claim 13, wherein:
   the pair of clamps includes a first clamp and a second clamp,
   each of the first clamp and the second clamp includes a grasping surface that is configured to contact the treated target that is grasped, and includes a back surface that faces a side opposite to the grasping surface,
   at least a part of the grasping surface of the first clamp is formed by the electrode, and
   the first clamp includes a heating body as the electric element, the heating body being provided on a back surface side of the first clamp with respect to the electrode, the heating body being configured to convert the second electric energy to the heat by being supplied with the second electric energy, and being configured to transmit the generated heat to the grasping surface through the electrode.

15. The energy treatment instrument of claim 14, wherein the electrode of the first clamp includes a ridge portion that extends from a proximal portion to a distal portion of the first clamp on the grasping surface, the ridge portion being configured to be abuttable on the grasping surface of the second clamp, in a state in which the pair of clamps are closed relative to each other.

16. An actuating method of an energy control device, the energy control device being configured to control a supply of energy to an energy treatment instrument, the energy treatment instrument being provided with an end effector that includes a pair of clamps that are openable and closable relative to each other, the end effector being configured to grasp a treated target between the clamps and the end effector including a pair of electrodes, and the energy treatment instrument including an electric element,
   first electric energy being supplied to the electrodes so as to pass a high-frequency current between the electrodes and through the treated target that is grasped between the clamps, and
   second electric energy being supplied to the electric element so as to actuate the end effector by generating heat in the end effector,
   the actuating method comprising:
      outputting the second electric energy to the electric element from a first time point so as to denature, from the first time point, the treated target by the heat generated by the actuation of the end effector;

judging whether or not the treated target entered a predetermined state after the first time point, the judgment being based on a dehydration state of the treated target; and executing one of:
  (i) starting an output of the first electric energy to the electrodes at a second time point, which is at the same time as or after the first time point, and then increasing the output of the first electric energy after the second time point based on judging that the treated target entered the predetermined state, and
  (ii) starting an output of the first electric energy to the electrodes after the first time point based on judging that the treated target entered the predetermined state.

* * * * *